(12) United States Patent
Goodlett et al.

(10) Patent No.: US 10,465,223 B2
(45) Date of Patent: Nov. 5, 2019

(54) METHODS FOR IDENTIFYING FUNGI

(71) Applicant: UNIVERSITY OF MARYLAND, BALTIMORE, Baltimore, MD (US)

(72) Inventors: David Goodlett, Baltimore, MD (US); Robert Ernst, Silver Spring, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 15/026,400

(22) PCT Filed: Oct. 9, 2014

(86) PCT No.: PCT/US2014/059853
§ 371 (c)(1),
(2) Date: Mar. 31, 2016

(87) PCT Pub. No.: WO2015/054468
PCT Pub. Date: Apr. 16, 2015

(65) Prior Publication Data
US 2016/0215322 A1 Jul. 28, 2016

Related U.S. Application Data

(60) Provisional application No. 61/888,577, filed on Oct. 9, 2013.

(51) Int. Cl.
| G01N 24/00 | (2006.01) |
| C12Q 1/04 | (2006.01) |
| G16B 35/00 | (2019.01) |
| G16C 20/60 | (2019.01) |
| G01N 33/92 | (2006.01) |

(52) U.S. Cl.
CPC ............... *C12Q 1/04* (2013.01); *G01N 33/92* (2013.01); *G16B 35/00* (2019.02); *G16C 20/60* (2019.02); *G01N 2333/37* (2013.01); *G01N 2560/00* (2013.01)

(58) Field of Classification Search
USPC ......................................................... 436/173
See application file for complete search history.

(56) References Cited

U.S. PATENT DOCUMENTS

| 2004/0234952 A1 | 11/2004 | Kallow et al. |
| 2012/0197535 A1 | 8/2012 | Goodlett et al. |
| 2013/0309712 A1 | 11/2013 | Maier |

FOREIGN PATENT DOCUMENTS

| WO | 01/92872 | 12/2001 |
| WO | 2005/085838 | 9/2005 |
| WO | 2010/100612 | 9/2010 |
| WO | 2012/069768 | 5/2012 |

OTHER PUBLICATIONS

Ejsing, C.S., et al., Automated Identification and Quantification of Glycerophospholipid Molecular Species by Multiple Precursor Ion Scanning, 2006, Analytical Chemistry, vol. 78(17), pp. 6202-6214.*

(Continued)

*Primary Examiner* — Xiaoyun R Xu
(74) *Attorney, Agent, or Firm* — Wenderoth, Lind & Ponack, L.L.P.

(57) ABSTRACT

Methods for identifying fungal species by analysis of fungal membrane lipids, such as glycerophospholipids, sphingolipids and sterols, using mass spectrometry ionization patterns are disclosed.

14 Claims, 8 Drawing Sheets

(56) References Cited

OTHER PUBLICATIONS

Guan, X.L., et al. Functional Interactions between Sphingolipids and Sterols in Biological Membranes Regulating Cell Physiology, 2009, Molecular Biology of the Cell, vol. 20, pp. 2083-2095.*

Hannich, J.T. et al. Distribution and Functions of Sterols and Sphingolipids, Cold Spring Harbor Perspectives in Biology, vol. 3, pp. 1-14 (Year: 2011).*

Kofeler et al., "Mass Spectrometry Based Lipidomics: An Overview of Technological Platforms", Metabolites, vol. 2, 19-38 (2012).

International Search Report dated Jan. 12, 2015 in application No. PCT/US2014/059853.

Extended European Search Report dated Mar. 27, 2017 in corresponding European Application No. 14852095.0.

Müller et al., "Combining sterol and fatty acid profiles for the characterization of fungi", Mycological Research, 98(6):593-603 (1994).

Valentine et al., "Direct surface analysis of fungal species by matrix-assisted laser desorption/ionization mass spectrometry", Rapid Communications in Mass Spectrometry, 16(14):1352-1357 (2002).

Cassagne et al., "Mould Routine Identification in the Clinical Laboratory by Matrix-Assisted Laser Desorption Ionization Time-of-Flight Mass Spectrometry", PLOS ONE, 6(12): 1-9 (2011).

Hettick et al., "Discrimination of *Aspergillus* isolates at the species and strain level by matrix-assisted laser desorption/ionization time-of-flight mass spectrometry fingerprinting", Analytical Biochemistry, 380(2):276-281 (2008).

\* cited by examiner

■ Complete match, identical organisms

▨ Low similarity and distinguishable by our method

METHODS FOR IDENTIFYING FUNGI

BACKGROUND

Rapid and accurate identification of microbes, such as fungi of medical importance, is needed to allow physicians to react and respond appropriately to infections, including those that are potentially life threatening. Systemic fungal infections, for example, have because a major cause of morbidity and mortality in immunocompromised patients.

Currently, microbe identification requires culture on solid medium or growth in liquid media under specific conditions of atmosphere, heat and humidity, followed by diagnostic analysis that may require additional rounds of replication in culture or purification of specific microbe products. At best, microbe identification requires many days during which patient health can be difficult to maintain or even rapidly deteriorate while the causative agent of the illness is ascertained. Thus, improved methods for microbe identification are needed.

SUMMARY OF THE INVENTION

In a first aspect, the invention provides methods for identifying fungi in a sample, comprising (a) obtaining precursor ion mass spectra (PIMS) data on precursor ions for one or more of (i) a fungal glycerophospholipid, (ii) a fungal sphingolipid, (iii) a fungal sterol, and (iv) precursors molecules thereof, from a sample containing fungi of interest;

(b) comparing the PIMS data to a counterpart database of (i) fungal glycerophospholipid PIMS data, (ii) fungal sphingolipid PIMS data, (iii) fungal sterol PIMS data, and/or (iv) precursor molecule PIMS data;

wherein the comparing is used to identify fungi in the sample.

As disclosed herein, the inventors have surprisingly discovered that the methods of the invention can be used, for example, to identify fungi in a sample and to distinguish between two or more fungi in the same sample. As such, the present invention will find wide use in a variety of diagnostic and research applications.

In one embodiment, the methods comprise comparing precursor ion m/z values and relative abundance of the precursor ions to the database of glycerophospholipid, sphingolipid, sterol, or precursor molecule PIMS data. In another embodiment, the methods further comprise fragmenting all or a subset of the precursor ions to produce a multiplexed set of ions, and obtaining mass spectra on all or a subset of the multiplexed set of ions (multiplexed mass spectra data), and wherein the comparing further comprises comparing the multiplexed mass spectra data to one or more of glycerophospholipid, sphingolipid, sterol, or precursor molecule multiplexed mass spectra data in the database to assist in identifying fungi in the sample. In a further embodiment, the methods further comprise fragmenting all or a subset of the precursor ions to produce a set of derived fragment ions, and obtaining mass spectra on all or a subset of the derived fragment ions ($MS^n$ data), and wherein the comparing further comprises sequentially comparing the $MS^n$ data to glycerophospholipid, sphingolipid, sterol, or precursor molecule $MS^n$ data in the database to assist in identifying fungi in the sample. In another embodiment, the methods further comprise searching the precursor ion and/or $MS^n$ data against a database of glycerophospholipid, sphingolipid, sterol, and precursor molecule signature ions to identify signature ions in the precursor ion and/or $MS^n$ data.

The methods may further comprise (i) searching neutral losses of signature ions in the $MS^n$ data against a theoretical neutral loss database to identify dissociation formulae;

(ii) proposing glycerophospholipid, sphingolipid, sterol, and/or precursor molecule candidate structures from fungi in the sample based on the dissociation formulae and the signature ions in the $MS^n$ data;

(iii) assigning a score to each glycerophospholipid, sphingolipid, sterol, and/or precursor molecule candidate structure based on correlation between theoretical and acquired $MS^n$ data, wherein candidate structures that meet or exceed a user-defined threshold are considered as accurate assignments.

In one embodiment, step (i) comprises (A) determining a neutral loss of every $MS^n$ spectrum's precursor ion in the corresponding $MS^{n-1}$ spectrum and searching against the theoretical neutral loss database; and (B) iteratively repeating step (A) until level $MS^1$ is reached; and wherein step (ii) comprises proposing the glycerophospholipid, sphingolipid, sterol, and/or precursor molecule structures from the fungi in the sample based on the integrating data from each $MS^n$ level.

In another embodiment, step (iii) comprises (A) fragmenting the glycerophospholipid, sphingolipid, sterol, and/or precursor molecule candidate structures by direct bond cleavage to produce fragmentations;

(B) combining the fragmentations into a reconstructed mass spectra representing the theoretical dissociation of the glycerophospholipid, sphingolipid, sterol, and/or precursor molecule candidate structures; and (C) assigning the score to each of the glycerophospholipid, sphingolipid, sterol, and/or precursor molecule candidate structure based on correlation between theoretical $MS^n$ spectra and the reconstructed mass spectra.

In one embodiment of the first aspect, the method further comprises:

(c) obtaining mass spectra data on precursor ions for fungal proteins in the sample;

(d) comparing the protein mass spectra data to a database of fungal protein precursor ion mass spectra data; wherein the comparing is used to help identify fungi in the sample.

In embodiments of the first aspect, the fungal glycerophospholipid is a fungal membrane glycerophospholipid, the fungal sphingolipid is a fungal membrane sphingolipid, and the fungal sterol is a fungal membrane sterol.

In one embodiment of the first aspect, the sample contains a single fungal species. In another embodiment, the sample contains two or more fungal species.

In a second aspect, the present invention provides methods for constructing libraries of glycerophospholipid, sphingolipid, sterol, and/or precursor molecule precursor ion and multiplexed mass spectra and/or $MS^n$ data, comprising (a) obtaining PIMS data on precursor ions for one or more of (i) a fungal glycerophospholipid, (ii) a fungal sphingolipid, (iii) a fungal sterol, and (iv) precursors molecules thereof obtained from a plurality of different fungi;

(b) determining precursor ion m/z values and relative ratios of precursor ion signals relative to each other;

(c) determining consensus values for the precursor ion m/z values and the relative ratios of the precursor ion signals relative to each other for a given fungi; and (d) storing the consensus values in a database as a feature of the fungal type.

In embodiments of the second aspect, the fungal glycerophospholipid is a fungal membrane glycerophospholipid, the fungal sphingolipid is a fungal membrane sphingolipid, and the fungal sterol is a fungal membrane sterol.

In embodiments of this aspect, the fungi is a fungal genera selected from the group consisting of *Candida, Aspergillus, Rhyzopus, Cryptococcus, Histoplasma, Pneumocystis, Stachybotrys, Sporothrix, Trichophyton, Microsporum, Blastomyces, Mucoromycotina, Coccidioides, Exserohilum, Cladosporium, Coccoides, Encephalitozoon, Encephalitozoon, Fusarium, Lichtheimia, Mortierella, Malassezia, Prototheca, Pythium, Rhodotorula, Fusarium, Thielaviopsis, Verticillium, Magnaporthe, Sclerotinia, Ustilago, Rhizoctonia, Puccinia, Armillaria, Botrytis, Blumeria, Mycosphaerella, Colletotrichum, Melampsora, Saprolegniasis, Ichthyosporidium, Exophiala, Branchiomycosis,* and *Penicillium.*

In embodiments of this aspect, the fungi is a fungal species selected from the group consisting of *Histoplasma capsulatum, Blastomyces dermatitidis, Coccidioides immitis, Paracoccidioides brasiliensis, Aspergillus fumigatus, Candida albicans, Cryptococcus neoformans, Magnaporthe grisea, Sclerotinia sclerotiorum, Phakospora pachyrhizi* and *Botrytis cinerea.*

DETAILED DESCRIPTION OF THE INVENTION

All references cited are herein incorporated by reference in their entirety. As used herein, the singular forms "a", "an" and "the" include plural referents unless the context clearly dictates otherwise. "And" as used herein is interchangeably used with "or" unless expressly stated otherwise. All embodiments of any aspect of the invention can be used in combination, unless the context clearly dictates otherwise.

In a first aspect, the present invention provides methods for identifying fungi in a sample, comprising (a) obtaining precursor ion mass spectra (PIMS) data on precursor ions for one or more of (i) a fungal glycerophospholipid, (ii) a fungal sphingolipid, (iii) a fungal sterol, and (iv) precursors molecules thereof, from a sample containing fungi of interest;

(b) comparing the PIMS data to a counterpart database of (i) fungal glycerophospholipid PIMS data, (ii) fungal sphingolipid PIMS data, (iii) fungal sterol PIMS data, and/or (iv) precursor molecule PIMS data; wherein the comparing is used to identify fungi in the sample.

As disclosed herein, the inventors have surprisingly discovered that the methods of the invention can be used, for example, to identify fungi and to distinguish between two or more fungi in sample. As such, the present invention will find wide use in a variety of diagnostic and research applications.

Figure 5:
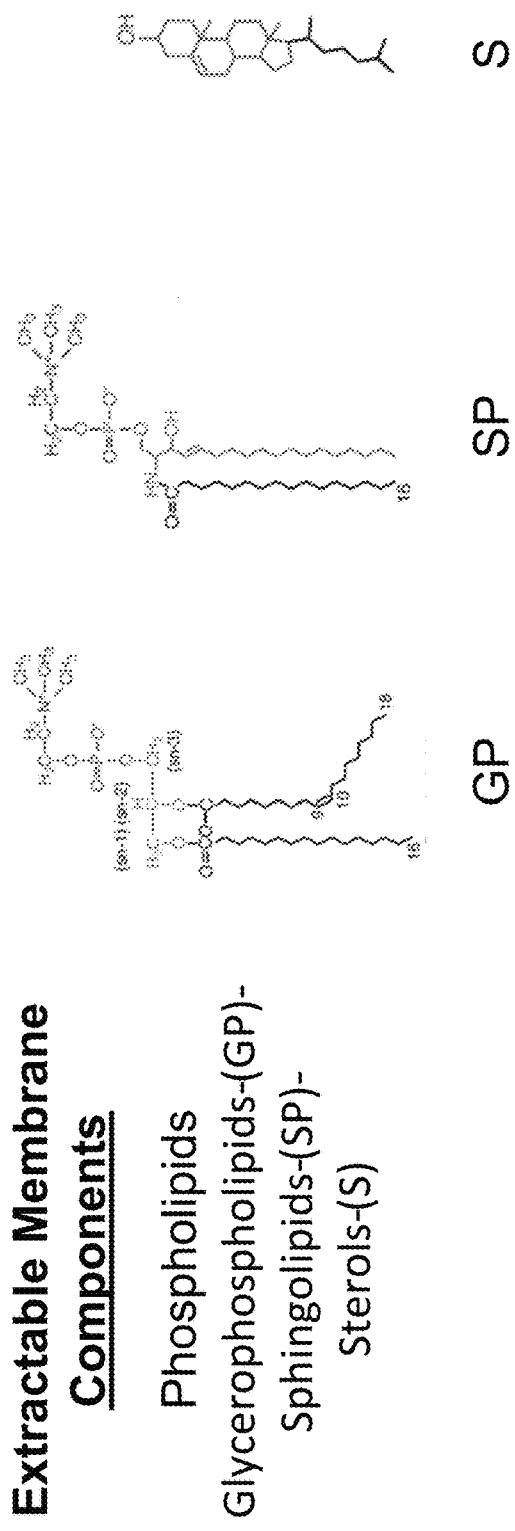
FIG. 5 shows representative fungal membrane glycerophospholipids, sphingolipids, and sterols.

The fungal cell wall composition is a dynamic structure that is unique for individual fungal species and functions to protect the cell from changes in environmental stresses. Based on studies in a number of fungi, the cell wall has been shown to be composed primarily of polysaccharides. In contrast, the plasma membrane contains a high fraction of extractable lipids, including sterols, sphingolipids, and glycerophospholipids (FIG. 5). It has been shown that different fungal species adapt to environmental stresses (osmolarity, temperature, growth medium) by altering the composition of the lipids in their membrane. Several factors involved in the maintenance of proper membrane fluidity are the type of fatty acyl chains (their length and unsaturation), the fraction of sterols and, to a lesser extent, the nature of the polar phospholipid head-groups (phosphocholine, phosphoethanolamine). Modifications to bacterial and fungal lipids are essential and represent species-specific chemical barcodes that may be used to phenotype the organisms as a supplement to or in place of current protein phenotypes.

Fungi can be identified and differentiated in any suitable sample of interest that is believed to contain fungi. The fungi may be dead or alive, as fungal membrane lipids are quite stable. Non-limiting examples of samples include, but are not limited to water samples (including but not limited to water samples from ponds, streams, lakes, oceans, seas, wastewater, reservoirs, drinking water, water distribution pipeline, etc.), body fluid samples (including but not limited to wound secretions/scrapings, blood, urine, sweat, saliva, vaginal secretions, sputum), beverage samples, liquid medicine samples, food samples, environmental samples (for example, from, medical centers such as linens, medical devices, etc.); pharmaceutical facilities (for example, from, manufacturing or processing lines); food production facilities; livestock facilities; solid waste samples, diagnostic samples, air, air filters, air duct and breath samples.

The sample can be used as obtained, or can be processed in any way suitable for use with the methods of the invention. In one embodiment, the methods comprise identifying fungi directly from a complex sample (i.e., no requirement for amplifying fungi present in the sample). In another embodiment, fungi are isolated from the sample, such as by streaking onto solid culture media or inoculating into liquid culture media, followed by growth for an appropriate period of time and use of individual colonies or a small aliquot for isolation of lipids, or for initiating a larger-scale culture (for example, an overnight liquid culture) which is then subjected to lipid isolation. It is within the level of skill in the art, based on the teachings herein, to determine an appropriate strategy for processing the sample for a specific use.

As used herein, "lipid" means lipids from fungi, such as cell wall lipids and cell membrane lipids. These lipids include, but are not limit to, glycerophospholipids, sphingolipids, and sterols. Thus, reference herein to fungal glycerophospholipids includes, but is not limited to, a fungal membrane glycerophospholipid; reference to fungal sphingolipids includes, but is not limited to, a fungal membrane sphingolipid; and reference to fungal sterols includes, but is not limited to, a fungal membrane sterol.

In one embodiment, fungal cells are placed in the mass spectrometer for analysis, with no purification of fungal lipids. In a preferred embodiment, the lipids (and precursors thereof) can be isolated from fungi in the sample using any suitable method that serves to maintain lipid structure. As used herein, "isolation" means that lipids are separated from their normal cellular environment. The methods do not require the use of purified lipids. In preferred embodiments, the lipids for use in the methods of the invention makes up at least 10% of the sample subjected to MS analysis; preferably at least 20%, 30%, 40%, 50%, 60%, 70%, 80%, 90%, 95%, 98%, 99%, or 100% of the sample subjected to MS analysis. Such isolation techniques are known to those of skill in the art, including but not limited to the use of various organic solvents (ex: phenol, chloroform, methanol, ethanol, etc.), ammonium hydroxide/isobutyric acid-based protocols, and microwave-assisted enzymatic digestion and detergent-free mild hydrolysis, as described below. For example, after extraction, lipids can be isolated from the phenol-based preparations using gentle hydrolysis, which preserves structural elements (e.g., phosphate groups and attached carbohydrate moieties) that are sensitive to harsh acid treatment, or directly for the ammonium hydroxide/isobutyric acid-based as it cleaves the glycosidic linkages within the lipid molecules.

It will be understood by those of skill in the art that methods for isolating lipids and their precursors may differ for fungi in different samples; some fungi may require additional growth time for the growth of colonies, and the membrane characteristics of a given fungi will affect extraction. Based on the teachings herein, it is within the level of skill in the art to determine the appropriate use of solvents, detergents, buffers, microwave power settings, time under irradiation, etc. to carry out the various types of lipid or precursor extraction.

The methods of the invention comprise obtaining precursor ion mass spectra (PIMS) data. As is known in the art, mass spectrometry (MS) is an analytical technique that measures the mass-to-charge ratio of charged particles, and can be used for determining the elemental composition of a sample or molecule and elucidating the chemical structures of molecules. MS comprises ionizing chemical compounds to generate charged molecules or molecule fragments and measuring their mass-to-charge ratios. In a typical MS procedure (a) a sample is loaded onto the MS instrument and undergoes vaporization; (b) the components of the sample are ionized by one of a variety of methods, resulting in the formation of ions; (c) the ions are separated according to their mass-to-charge ratio in an analyzer by electrical and magnetic fields; (d) the ions are detected, often by a quantitative method; and (e) the ion signal is processed into mass spectra. Suitable instruments for carrying out MS thus typically comprise (a) an ion source, which can convert gas phase sample molecules into ions (or, in the case of electrospray ionization, move ions that exist in solution into the gas phase); a mass analyzer, which sorts the ions by their masses by applying electromagnetic fields; and (c) a detector, which measures the value of an indicator quantity and thus provides data for calculating the abundances of each ion present.

Any suitable MS instrument can be used in the methods of the invention, including, but not limited to, floor model MS instruments, bench-top MS instruments, and miniaturized MS instruments. Selecting an appropriate MS instrument and protocol can be accomplished by one of skill in the art based on the teachings herein. Non-limiting MS techniques that can be used to carry out the methods of any embodiment or combination of embodiments of the present invention include, but are not limited to, matrix-assisted laser desorption ionization time-of flight MS (MALDI-TOF-MS) platforms, tandem MS, MALDI-TOF-TOF-MS, infusion-based electrospray ionization (ESI) coupled to ion trap tandem mass spectrometry (ITMS"), MALDI-ITMS" and any of the many so-called ambient ionization methods such as surface acoustic wave nebulization (SAWN) technology, including SAWN on any mass analyzer (e.g. quadrupole TOF-MS (QTOF) or SAWN-ion trap (IT) MS). Other examples of ambient ionization methods include DESI and DART as well as derivations thereof such as REIMS used in surgeries, but there are numerous such methods available, as will be understood by those of skill in the art.

Surface acoustic waves (SAWs) are Rayleigh waves, and are generated by the application of a voltage across a piezoelectric material, causing a mechanical displacement of the uppermost layer of the chip, which propagates as a "ripple" across the surface of the wafer. At the appropriate frequency, surface acoustic waves can be used to atomize droplets pipetted onto the surface of a lithium niobate wafer. It has previously been shown that the SAW nebulized (SAWN) aerosol contains charged molecules that could be sampled by MS to record usable $MS^1$ and $MS^2$ spectra (WO2011/060369). In fact, SAWN generates multiply charged ions similar to those of ESI that can be easily subjected to $MS^n$. The advantage of lipid analysis by SAWN over MALDI and ESI are three-fold: 1) ionization occurs from a planar device, like MALDI, that circumvents clogging of capillaries and thus facilitating higher throughput and ease of use by non-experts, 2) it is less energetic than ESI and MALDI making it more likely that the native chemical signature we seek to measure will be intact on transfer to the MS, and 3) no chemical matrix is required as is the case with MALDI such that mass spectra free of matrix-based chemical noise are produced down to the low m/z region where lipids of interest to this proposal are detected. A planar SAWN device provides the ease of use of MALDI, i.e. a planar surface where samples are simply pipetted, but without need for a matrix that can obscure ions of interest and combines this with the performance of ESI, i.e. multiply charged precursor ions that can be used in, for example, hierarchical tandem mass spectrometry ($MS^n$), as described below.

As used herein, "precursor ions" are ions of a starting molecule (lipid and/or precursors thereof) generated during MS. Such precursor ions may also be referred to as $MS^1$ ions. As will be understood by those of skill in the art, MS may result in a large number of precursor ions from a given starting molecule. Obtaining the PIMS data does not require obtaining PIMS data of all $MS^1$ ions. Thus, in various embodiments, obtaining the PIMS data comprises obtaining PIMS data on 1, 2, 3, 4, 5, 6, 7, 8, 9, 10, 11, 12, 13, 14, 15, 16, 17, 18, 19, 20, 21, 22, 23, 24, or more $MS^1$ ions. In one non-limiting example, the method comprises obtaining the PIMS data for the 1, 2, 3, 4, 5, 6, 7, 8, 9, 10, 11, 12, 13, 14, 15, 16, 17, 18, 19, 20, 21, 22, 23, 24, or more $MS^1$ ions, such as the most predominant ions. In another embodiment, the method comprises obtaining the PIMS data on all $MS^1$ ions.

The PIMS data provides information on (a) the m/z values of the precursor ions generated, which represents (or reads) a "barcode" for the fungal lipids (such as fungal membrane lipids) in the sample; and (b) the relative abundance of the precursor ions generated. The method further comprises comparing the PIMS data to a database of fungal lipid precursor ion mass spectra data, to permit identification of fungi present in the sample based on the comparison. For example, fungal identifications may occur by reading out simple phenotypes of two measured components for each sample: 1) precursor ion m/z values (mass to charge ratio) which can be used for determining the elemental composition of a sample or molecule and elucidating the chemical structures of molecules, 2) the normalized, relative abundance of these precursor ions, which may represent more subtle differences in the fungal signature, such as environmental factors and 3) by conducting hierarchical tandem mass spectra on all or a select set of PIMS ions to reveal differences and complexity under $MS^1$ ions composed of multiple entities all with different chemical configurations but the same $MS^1$ value commonly referred to as isobars.

In one embodiment using purified fungal lipids, including fungal membrane lipids, obtaining PIMS data on precursor ions comprises selecting peaks between about 1000 m/z and about 2200 m/z; in other embodiments, between about 1100 m/z and about 2100 m/z, or between about 1200 m/z and about 2000 m/z. These embodiments focus the analysis on ions with a mass to charge ratio likely to be of most relevance for the analysis. As will be understood by those of skill in the art, the m/z ranges can vary above or below these values, depending on all relevant factors in a given MS assay (such as degree of purification, instrument, etc.). In embodiments where unpurified lipid samples are used, the m/z ranges may be approximately 10 fold higher than those discussed above (i.e., between about 10,000 m/z and about 22,000 m/z).

The methods may further comprise various techniques for data processing, as are within the level of skill in the art based on the teachings herein. For example, the methods may comprise weighting and scaling of spectral peaks using any suitable technique. In another non-limiting embodiment, spectral peaks may be binned as a means to reduce costs and computational requirements.

The methods of the invention further comprise comparing the PIMS data to a database of fungal lipid precursor ion mass spectra data, wherein the comparing is used to identify fungi in the sample. The database may be of any suitable type for a given application. In one embodiment, the database may comprise or consist of fungal lipid precursor ion MS data previously obtained from a single fungal species (and may include precursor ion MS data a variety of sub-species); this embodiment can be used, for example, in methods designed to determine if a specific fungus of interest is present in the sample. In another embodiment, the database may comprise or consist of fungal lipid precursor ion MS data previously obtained from a plurality of fungi of interest. In one such embodiment, the database contains fungal lipid precursor ion MS data previously obtained from a plurality of fungi. In another such embodiment, the database may comprise or consist of precursor ion fungal lipid MS data previously obtained from a one or more fungi known to develop anti-fungal resistance, wherein the previously obtain MS data includes data from anti-fungal-resistant strains and non-anti-fungal resistant strains of the fungi. As will be understood by those of skill in the art, there are many such variations of databases that can be used in the methods of the invention. A suitable database for use will depend on the specifics of the methods to be carried out, and can be determined by one of skill in the art based on the teachings herein. In another embodiment, the database may comprise or consist of any of the database libraries disclosed herein.

In another embodiment, the database may comprise or consist of fungal lipid precursor ion MS data previously obtained from one or more (or all) of the following groups of genera of important fungi, species thereof, or sub-species thereof. *Human and Livestock Fungal Pathogens: Candida, Aspergillus, Rhyzopus, Cryptococcus, Histoplasma, Pneumocystis, Stachybotrys, Sporothrix, Trichophyton, Microsporum, Blastomyces, Mucoromycotina, Coccidioides, Exserohilum, Cladosporium*. Livestock Fungal Pathogens: *Coccoides, Encephalitozoon, Encephalitozoon, Fusarium, Lichtheimia, Mortierella, Malassezia, Prototheca, Pythium, Rhodotorula*. Crop Fungal Pathogens: *Fusarium, Thielaviopsis, Verticillium, Magnaporthe, Sclerotinia, Ustilago, Rhizoctonia, Puccinia, Armillaria, Botrytis, Blumeria, Mycosphaerella, Colletotrichum, Melampsora*. Fish Fungal Pathogens: *Saprolegniasis, Ichthyosporidium, Exophiala, Branchiomycosis*. Others: *Penicillium*. Representative fungal species include *Histoplasma capsulatum, Blastomyces dermatitidis, Coccidioides immitis, Paracoccidioides brasiliensis, Aspergillus fumigatus, Candida albicans, Cryptococcus neoformans, Magnaporthe grisea, Sclerotinia sclerotiorum, Phakospora pachyrhizi* and *Botrytis cinerea*.

The methods of the invention may be used to detect single fungal cells present in a sample. In various embodiments, at least $10^2$, $10^3$, $10^4$, $10^5$, or $10^6$, fungal cells are present in the sample.

The data included in the databases includes at least precursor ion m/z values for fungal lipid molecules in the fungi represented in the database. The data may also include the normalized, relative abundance of these precursor ions, as well as data regarding the MS technique used to generate the data. In a preferred embodiment, the MS technique used to generate the PIMS data from the sample is the same as the MS technique used to generate the data in the database. The data may include limited or exhaustive hierarchical tandem mass spectrometry data (as embodied in *J Am Soc Mass Spectrom*. 22(5):856-66 (2011)) used to define structures or define subtle differences between species on all or a select set of PIMS ions. The data may further comprise structural information for the lipids present in fungi or sub-species thereof represented in the database.

The database may comprise a single database, or one or more databases that can be separately accessed and may be integrated, as discussed in more detail below.

In another embodiment, the comparison comprises a classification system to provide a score for identification. For example, each database entry can include a probability-based score. This score, perhaps along with other information, can be used to identify an ion, spectrum, lipid or lipid precursor. Any such suitable classification system can be used to provide a score such as a probability based score, and it is well within the level of those of skill in the art to determine an appropriate system based on the teachings herein.

Figure 7:
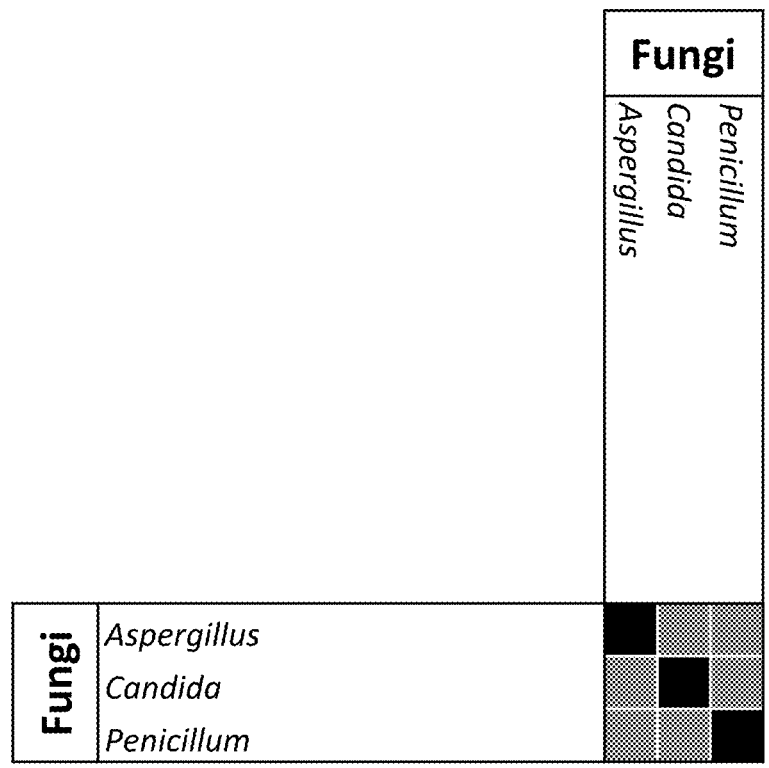
FIG. 7 shows a heat map demonstrating fungal identification from MALDI-TOF-MS data of fungal lipid extracts. Dot-product comparison of MALDI-TOF MS1 spectra of fungal lipid extracts shows lipids are unique for the species analyzed. Dot-product scores are normalized to values between 0: no match (dark gray), to 1: a perfect match (black). Shades in between indicate that species are similar, but unique.

Any type of comparison of the PIMS data to the database MS data can be used to identify fungi in the sample. For example, any means of comparing the lipid and/or precursor ion m/z values in the sample to the m/z values in the database can be used; similarly, any means of comparing the relative abundance of such precursor ions generated from fungal lipids in the sample to the data in the database can be used. In one non-limiting embodiment, the comparison may comprise a dot-product comparison of spectra incorporating m/z values and (optionally) their relative intensities. In another embodiment, a heat map comparison of spectra incorporating m/z values and (optionally) their relative intensities can be used. An example heat map is depicted in FIG. 7. It is well within the level of those of skill in the art to determine an appropriate comparison technique based on the teachings herein.

The methods of the invention can be used to identify any fungal species or sub-species in a sample. Further, the methods can be used to identify multiple fungal species and/or sub-species from a given sample.

In various non-limiting embodiments, the methods can be used to identify one or more of fungal genera, species thereof, or sub-species thereof, including but not limited to the following genera: *Candida, Aspergillus, Rhyzopus, Cryptococcus, Histoplasma, Pneumocystis, Stachybotrys, Sporothrix, Trichophyton, Microsporum, Blastomyces, Mucoromycotina, Coccidioides, Exserohilum, Cladosporium, Coccoides, Encephalitozoon, Encephalitozoon, Fusarium, Lichtheimia, Mortierella, Malassezia, Prototheca, Pythium, Rhodotorula, Fusarium, Thielaviopsis, Verticillium, Magnaporthe, Sclerotinia, Ustilago, Rhizoctonia, Puccinia, Armillaria, Botrytis, Blumeria, Mycosphaerella, Colletotrichum, Melampsora, Saprolegniasis, Ichthyosporidium, Exophiala, Branchiomycosis*, and *Penicillium*. Representative fungal species include *Histoplasma capsulatum, Blastomyces dermatitidis, Coccidioides immitis, Paracoccidioides brasiliensis, Aspergillus fumigatus, Candida albicans, Cryptococcus neoformans, Magnaporthe grisea, Sclerotinia sclerotiorum, Phakospora pachyrhizi* and *Botrytis cinerea*.

As shown in the examples that follow, analysis of $MS^1$ spectra was used to demonstrate the ability of fungal lipid $MS^1$ data to distinguish between fungal genera at high sensitivity, accuracy, and specificity.

In another embodiment, the method further comprises fragmenting all or a subset of the precursor ions to produce a multiplexed set of ions, and obtaining mass spectra on all or a subset of the multiplexed set of ions (multiplexed mass spectra data), and wherein the comparing further comprises comparing the multiplexed mass spectra data to fungal lipid multiplexed mass spectra data in the database to assist in identifying fungi in the sample. Those of skill in the art will understand the types of mass spectrometry devices that are most suitably used with this embodiment of the invention. Any MS device that can fragment ions can produce multiplexed mass spectra data. For example, the simplest form of an MS is an ionization device and a mass analyzer and detector. One can modify the way ions are made going from "soft" where mostly MS1 ions are recorded to "hard" where mostly all of the MS1 are fragmented to produce a multiplexed mass spectra spectrum. In another embodiment, an ESI-TOF-MS device can be used (see Proteomics 3:847-850 (2003)).

As used herein, "multiplexed mass spectra" refers to fragmentation of all $MS^1$ ions, or a subset of ions. See, for example, *Nature Methods* 2004 Oct. 1(1):39-45. This embodiment can be used, for example, if the $MS^1$ data is inconclusive in identifying fungi present in the sample, and provides a multiplex approach that reveals additional information of fungal lipid structure.

In various embodiments, obtaining the multiplexed mass spectra comprises obtaining multiplexed mass spectra on 1, 2, 3, 4, 5, 6, 7, 8, 9, 10, 11, 12, 13, 14, 15, 16, 17, 18, 19, 20, 21, 22, 23, 24, or more multiplexed ions. In one non-limiting example, the method comprises obtaining the multiplexed mass spectra for the 1, 2, 3, 4, 5, 6, 7, 8, 9, 10, 11, 12, 13, 14, 15, 16, 17, 18, 19, 20, 21, 22, 23, 24, or more of the most abundant multiplexed ions. In another embodiment, the method comprises obtaining the multiplexed mass spectra on all multiplexed ions.

The multiplexed mass spectra data provides similar information on the multiplexed ions as did the PMIS on the precursor ions, including but not limited to information on (a) the m/z values of the multiplexed ions assessed; and (b) the relative abundance of the multiplexed ions generated. Similarly, the database(s) to be used in this embodiment would further comprise previously obtained multiplexed mass spectra data similar to that present in the database for the PIMS data, including but not limited to multiplexed ion m/z values for fungal lipid molecules in the fungus represented in the database. The data may also include the normalized, relative abundance of these multiplexed ions, scoring information, as available, for the multiplexed ions, as well as data regarding the MS technique used to generate the data.

In one embodiment, obtaining multiplexed mass spectra on multiplexed ions comprises selecting peaks between about 1000 m/z and about 2200 m/z; in other embodiments, between about 1100 m/z and about 2100 m/z, or between about 1200 m/z and about 2000 m/z. These embodiments focus the analysis on multiplexed ions with a mass to charge ratio likely to be of most relevance for the analysis.

In another embodiment, the methods further comprise fragmenting all or a subset of the precursor ions to produce a set of derived fragment ions, and obtaining mass spectra on all or a subset of the derived fragment ions ($MS^n$ data), and wherein the comparing further comprises sequentially comparing the $MS^n$ data to fungal lipid $MS^n$ data in the database to assist in identifying fungi in the sample. This embodiment can be used, for example, where PMIS and/or multiplexed mass spectra data is inconclusive, or where more detailed structural information on the relevant lipid species is desirable. For example, this embodiment can be used to determine new fungal lipid structures. Thus, this embodiment can be used, for example, to identify new biomarkers of specific fungi, as well as biomarkers of antifungal resistant fungal strains. Those of skill in the art will understand the types of mass spectrometry devices that are most suitably used with this embodiment of the invention. For example, an ion trap can be used to obtain full $MS^n$ spectra, while other tandem mass spectrometers (i.e., those with more than one mass analyzer, including but not limited to triple quad MS, QTOF MS, and Qtrap MS) can typically obtain $MS^3$ spectra.

As used herein, "derived fragment ions" are ions fragmented from the precursor ions; the first generation of such ions ($MS^2$) are fragmented from the $MS^1$ ions; the second generation of such derived fragment ions ($MS^3$) are fragmented from the $MS^2$ ions, etc. The process is iterative, with $MS^n$ representing the number of generations. Thus, in one embodiment, the $MS^n$ spectra data is obtained for at least two generations, $MS^1$ and $MS^2$, of derived fragment ions, and compared to fungal lipid $MS^1$ and $MS^2$ spectra in the database. In another embodiment, the $MS^n$ spectra data is obtained for at least generations, $MS^1$, $MS^2$, and $MS^3$, of derived fragment ions, and compared to fungal lipid $MS^1$, $MS^2$, and $MS^3$ spectra in the database. The methods can be repeated to any desired "n" value of derived fragment ions (2, 3, 4, 5, 6, etc.). This embodiment is sequential, in that each successive generation of derived fragment ion derived from a single precursor ion can be compared against the database, in contrast to the multiplexed mass spectra embodiment, where all subsequent generations of fragmented ions (or subsets thereof) are compared against the database simultaneously. For example, in one embodiment, $MS^1$ spectra are compared to the database and, if needed (i.e., no difference seen, or not enough difference, etc.), $MS^2$ spectra are compared to the database. Similarly, $MS^3$ and further spectra can be obtained and compared to the database until a desired end-point is obtained (such as a difference seen either in chemical structure or relative abundance (from ion intensity values present in all spectra) of things all with the same structure). Each level of $MS^n$ data reveals new structural details of the lipids that allow more refined structures to be defined.

In various embodiments, obtaining the $MS^n$ data comprises obtaining $MS^n$ mass spectra on 1, 2, 3, 4, 5, 6, 7, 8, 9, 10, 11, 12, 13, 14, 15, 16, 17, 18, 19, 20, 21, 22, 23, 24, or more $MS^n$ ions; the number can differ from one generation of derived fragment ions to another, as deemed suitable for a given purpose. In one non-limiting example, the method comprises obtaining the $MS^n$ mass spectra for the 1, 2, 3, 4, 5, 6, 7, 8, 9, 10, 11, 12, 13, 14, 15, 16, 17, 18, 19, 20, 21, 22, 23, 24, or more of the most abundant $MS^n$ ions. In another embodiment, the method comprises obtaining the $MS^n$ mass spectra on all $MS^n$ ions The $MS^n$ data provides similar information on the $MS^n$ ions as did the PMIS on the precursor ions, including but not limited to information on (a) the m/z values of the $MS^n$ ions assessed; and (b) the relative abundance of the $MS^n$ ions generated. Similarly, the database to be used in this embodiment would further comprise previously obtained $MS^n$ data similar to that present in the database for the PIMS data, including but not limited to $MS^n$ ion m/z values for fungal lipid molecules in the fungi represented in the database. The data may also include the normalized, relative abundance of these $MS^n$ ions, as well as data regarding the MS technique used to generate the data.

In a further embodiment, that can be combined with any embodiment or combination of embodiments herein, the method further comprises searching the precursor ion and/or $MS^n$ data against a database of fungal lipid signature ions to identify signature ions in the precursor ion and/or $MS^n$ spectra. As used herein, "signature ions" are unique ions that help hypothesize the molecule's structure. In this embodiment, the database may comprise one database of previously identified signature ions for fungi represented in the database, and a second database comprising the precursor ion and/or $MS^n$ ion mass spectra data. In this non-limiting example, fungal lipids are subjected to a hierarchical tandem mass spectrometry ($MS^n$) strategy that generates $MS^2$ and higher tandem mass spectra for each significant precursor ion detected in an $MS^1$ scan. Structures are assigned by the method which first searches a theoretical signature ion (TSI) database to detect signature ions and then confirms these by comparison to a database of expected theoretical neutral losses (TNL) from which a chemical formula and structure is derived.

Tandem mass spectrometry involves multiple steps of mass spectrometry selection, with some form of fragmentation occurring in between the stages. Exemplary tandem MS techniques suitable for use with the present claims include, but are not limited to, those disclosed in Shaffer et al. in the Journal of the American Society for Mass Spectrometry (JASMS), June 2007, Vol. 18, No. 6, pp. 1080-1092.

In a further embodiment, the comparing comprises (i) searching neutral losses of signature ions in the $MS^n$ data against a theoretical neutral loss database to identify dissociation formulae;

(ii) proposing fungal lipid candidate structures from fungi in the sample based on the dissociation formulae and the signature ions in the $MS^n$ data;

(iii) assigning a score to each fungal lipid candidate structure based on correlation between theoretical and acquired $MS^n$ data, wherein candidate structures that meet or exceed a user-defined threshold are considered as accurate assignments.

As used herein, dissociation formulae are the pathway(s) of dissociation of a precursor ion.

In this embodiment, the database comprise, for example, a database based on the interpretation of fungal lipid fragmentation rules in tandem mass spectra which includes phosphate patterns as well as fatty acid and monosaccharide substituents. Direct bond cleavages of fungal lipid structures can be considered as the general template for fragmentation and structural inference. In a further embodiment, each database may comprise two sub-databases (or may comprise two separate but connected databases) for: (1) theoretical signature ions (TSI) and (2) theoretical neutral losses (TNL). For example, the observed sterol signature ions can be determined from the conserved characteristic of sterols and named according to nomenclature known in the art. Based on the observed fragmentation templates of sterol, signature ions can be calculated and compared to the theoretical signature ion (TSI) database. In a further embodiment, any mass spectra without any identifiable signature ions are discarded prior to comparing to the database.

To increase the structural diversity of fungal lipids represented in the TSI database, a user-defined carbon range of fatty acids can be applied (for example, 12:0 to 20:0 fatty acids). By systematically altering the fatty acid side chain lengths and positions, all possible signature ions can be computed, if desired, and incorporated into the TSI database. To facilitate structure assignment, neutral losses of signature ions can be calculated and put in the theoretical neutral loss (TNL) database. Additionally, common observed neutral losses that come from direct bond cleavages of lipids other than cleavages of signature ions can also be included in the TNL database. Similarly, to increase the structural diversity covered by TNL databases, fatty acid compositions of TNL can be systematically altered within the user-defined carbon range.

In this embodiment, acquired $MS^n$ data can be searched against the TSI database to find possible signature ions and spectra without any identifiable signature ions can be discarded. Any identified signature ions suggest formulae corresponding to the reducing and/or non-reducing portions of the selected lipid. By subtracting the mass of signature ions from their precursors, the neutral losses of signature ions can be subsequently calculated and searched against the TNL database. The combination of signature ions and matched neutral losses may be used to provide a preliminary candidate structure.

In a further embodiment, searching neutral losses of signature ions in the $MS^n$ data against a theoretical neutral loss database to identify dissociation formulae comprises (A) determining a neutral loss of every $MS^n$ spectrum's precursor ion in the corresponding $MS^{n-1}$ spectrum and searching against the theoretical neutral loss database; and (B) iteratively repeating step (A) until level $MS^1$ is reached; and wherein step (ii) comprises proposing the fungal lipid structures from the fungi in the sample based on the integrating data from each $MS^n$ level.

In this embodiment, the calculated neutral losses of all the ions in each spectrum can also be searched against the TNL database to provide desired information for spectrum annotation (i.e., a lipid-spectrum match (LSM). After preliminary structures are assigned, neutral loss of one or more (or every) $MS^n$ spectrum's precursor ion can be calculated in the corresponding $MS^{n-1}$ spectrum and searched against the TNL database again to, for example, identify the possible dissociation patterns. The method may proceed iteratively until the $MS^1$ level is reached. The final structures can be deduced, for example, by integrating the information gained from the different levels of $MS^n$ data.

In another embodiment, assigning a score to each fungal lipid candidate structure based on correlation between theoretical and acquired $MS^n$ spectra comprises (A) fragmenting the fungal lipid candidate structures by direct bond cleavage to produce fragmentations;

(B) combining the fragmentations into a reconstructed mass spectra representing the theoretical dissociation of the fungal lipid candidate structures; and (C) assigning the score to each of the fungal lipid candidate structure based on correlation between theoretical $MS^n$ spectra and the reconstructed mass spectra.

In this embodiment, for every LSM, a hypothetical fungal lipid structure can be fragmented in silico based primarily on direct bond cleavages, including glycosidic bond cleavages (i.e. A/X, B/Y, C/Z type ions), losses of O- and N-linked acyl chains, losses of phosphate, losses of monosaccharide and perturbations representing combined losses. Fragmentations can, for example, then be combined into a reconstructed mass spectrum representing the theoretical dissociation of the candidate structure.

In another embodiment, an X-score may be applied to a lipid-spectrum match (LSM) to evaluate the closeness of fit between one or more acquired $MS^n$ spectrum and a theoretical tandem mass spectrum. The peak intensity of each reconstructed mass spectrum can, for example, be assigned a Boolean value where 1 represents, for example, the existence of a fragmentation of such m/z value. The X-score between the acquired mass spectrum and the reconstructed mass spectrum of hypothetical structure can be measured using any suitable scoring scheme, including but not limited to those disclosed in the examples below.

In one embodiment, each X-score calculation is a scalar dot product between reconstructed mass spectrum x and the preprocessed acquired mass spectrum y' with $\tau$ is the correction factor.

In a further embodiment, the methods may comprise use of a target-decoy strategy, for example, generating decoys by shuffling the candidate fungal lipid structures on-the-fly while analyzing each $MS^n$ spectrum. In one embodiment, such shuffling only occurs on the position and length of fungal lipid fatty acid side chains. This approach ensures that every decoy fungal lipid exhibits precisely the same molecular composition and mass as the target (i.e., candidate) fungal lipid structures. X-score of both candidate and decoy LSM can then be calculated to help evaluate the significance.

The methods of any embodiment or combination of embodiments of the invention can be used alone, or in combination with other fungal identification methods, such as those based on protein MS patterns. Thus, in another embodiment, the methods comprise obtaining mass spectra data on precursor ions for fungal proteins in the sample; comparing the protein mass spectra data to a database of fungal protein precursor ion mass spectra data; wherein the comparing is used to help identify fungi in the sample. In a further embodiment, the sample is processed to obtain fungal lipids together with protein using a standard protocol that maintains the pH of the sample between about 4 to 5, such as a pH of about 4.5, for the portion of the sample processing for fungal lipid isolation. In one exemplary embodiment, such a technique would comprise contacting a fungal pellet with sodium acetate (such as 5-20 ml), or any other suitable treatment resulting in a sample pH of about 4.5 with or without heating, and mixing to resuspend the fungi. Next, acetonitrile is added (such as about 5-20 ml) and the sample mixed, followed by centrifugation (such as at about 25,000 g for about 2 minutes) to obtain the supernatant for MS analysis. In another embodiment, the fungal sample is split into two samples, with a first sample pelleted and treated as above, and a second sample treated similarly, except that the sodium acetate is replaced with formic acid. In this embodiment, the first sample can be used for fungal lipid analysis and the second sample can be used for protein analysis. In a further embodiment, the sample is treated via the sodium acetate procedure and a portion of the sample is used for fungal lipid analysis, and the rest of the sample is treated with formic acid for protein analysis.

In this embodiment, the methods of the present invention can be used in combination with protein MS analysis to, for example, improve the efficiency of the protein MS analysis. One embodiment of such protein MS analysis is the Bruker MALDI Biotyper™ mass spectrometer platform (Bruker Daltonics) See, for example, Sauer et al., PLoS ONE 3(7): e2843. doi:10.1371/journal.pone.0002843. The methods of the present invention provide improved accuracy in fungal identification compared to protein-based MS techniques (or in combination with protein-based MS techniques).

Example Computing Environment

Results of a comparison between one or more input spectra data generated by a mass spectrometer or similar device (e.g., PIMS, multiplexed mass spectra, $MS^n$ spectra data) and one or more stored spectra data (e.g., spectra data stored as in a database) can be carried out in an automated fashion using a computing device acting as a "spectra identifier."

Upon completion, content related the results of the comparison can be generated by the spectra identifier. For example, the content can include graphs, images, alphanumeric, and/or video content preferably displayed to a user via a graphical user interface on either the spectra identifier or a client device.

Figure 1:
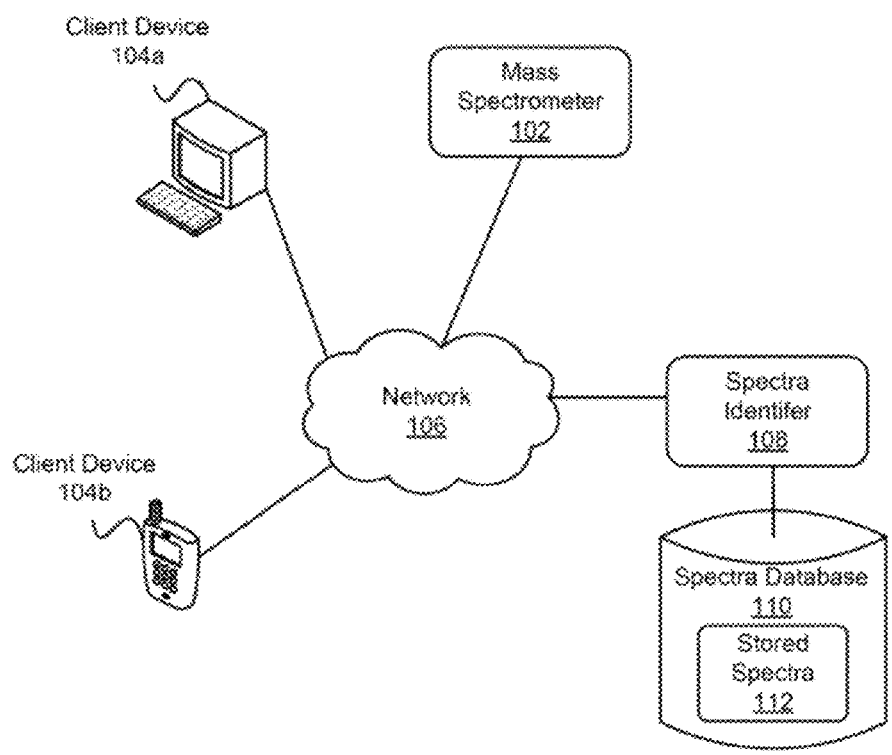
FIG. 1 shows spectral identifier 108 configured to communicate, via network 106, with mass spectrometer 102 and client devices 104a, 104b.

For example, FIG. 1 shows spectra identifier 108 configured to communicate, via network 106, with mass spectrometer 102 and client devices 104a, 104b. Network 106 may correspond to a LAN, a wide area network (WAN), a corporate intranet, the public Internet, or any other type of network configured to provide a communications path between networked computing devices. The network 106 may also correspond to a combination of one or more LANs, WANs, corporate intranets, and/or the public Internet.

Although FIG. 1 only shows two client devices, distributed application architectures may serve tens, hundreds, or thousands of client devices. Moreover, client devices 104a and 104b (or any additional client devices) may be any sort of computing device, such as an ordinary laptop computer, desktop computer, network terminal, wireless communication device (e.g., a cell phone or smart phone), and so on. In some embodiments, client devices 104a and 104b can be dedicated to MS and/or fungal research. In other embodiments, client devices 104a and 104b can be used as general purpose computers that are configured to perform a number of tasks and need not be dedicated to MS or fungal research. In still other embodiments, the functionality of spectra identifier 108 and/or spectra database 110 can be incorporated in a client device, such as client devices 104a and/or 104b. In even other embodiments, the functionality of spectra identifier 108 and/or spectra database 110 can be incorporated into mass spectrometer 102.

Mass spectrometer 102 can be configured to receive an input material, e.g. glycerophospholipid, sphingolipid, and/or sterol, and generate one or more spectra as output. For example, mass spectrometer 102 can be an electrospray ionization (ESI) tandem mass spectrometer or a SAWN-based mass spectrometer or a MALDI mass spectrometer. In some embodiments, the output spectra can be provided to another device, e.g., spectra identifier 108 and/or spectra database 110, perhaps to be used as an input to the device. In other embodiments, the output spectra can be displayed on mass spectrometer 102, client devices 104a and/or 104b, and/or spectra identifier 108.

Spectra identifier 108 can be configured to receive, as an input, one or more spectra from mass spectrometer 102 and/or client device(s) 104a and/or 104b via network 106. In some embodiments, spectra identifier can be configured to directly receive input spectra via keystroke, touchpad or similar data input to spectra identifier 108, hard-wired connection(s) to mass spectrometer 102 and/or client device(s) 104a and/or 104(b), accessing storage media configured to store input spectra (e.g., spectra database 110, flash media, compact disc, floppy disk, magnetic tape), and/or any other technique to directly provide input spectra to spectra identifier 108.

The one or more input spectra can include, for example, a $MS^n$ sequence of n related spectra from a given input material. Each of the n related spectra can relate to one or more different ions and/or neutral fragments of the input material.

Spectra identifier 108 can be configured to generate results of spectra identification by comparing one or more input spectra to stored spectra 112. For example, stored spectra 112 can be known precursor ion mass spectra (PIMS) data, multiplexed ion mass spectrometry spectra data, or $MS^n$ data. As shown in FIG. 1, stored spectra 112 can reside in spectra database 110. When performing spectra identification, spectra identifier 108 can access and/or query spectra database 110 to retrieve part or all of stored spectra 112. In some embodiments, spectra identifier 108 can perform the comparison task directly; while in other embodiments, part or all of the spectra identification task can be performed by spectra database 110, perhaps by executing one or more query language commands upon stored spectra 112.

While FIG. 1 shows spectra identifier 108 and spectra database 110 directly connected, in other embodiments, spectra identifier 108 can include the functionality of spectra database 110, including storing stored spectra 112. In still other embodiments, spectra identifier 108 and spectra database 110 can be connected via network 106.

Upon identifying the input spectra, spectra identifier 108 can be configured to provide content at least related to results of spectra identification, as requested by client devices 104a and/or 104b. The content related to results of spectra identification can include, but is not limited to, web pages, hypertext, scripts, binary data such as compiled software, images, audio, and/or video. The content can include compressed and/or uncompressed content. The content can be encrypted and/or unencrypted. Other types of content are possible as well.

Computing Device Architecture

Figure 2A:
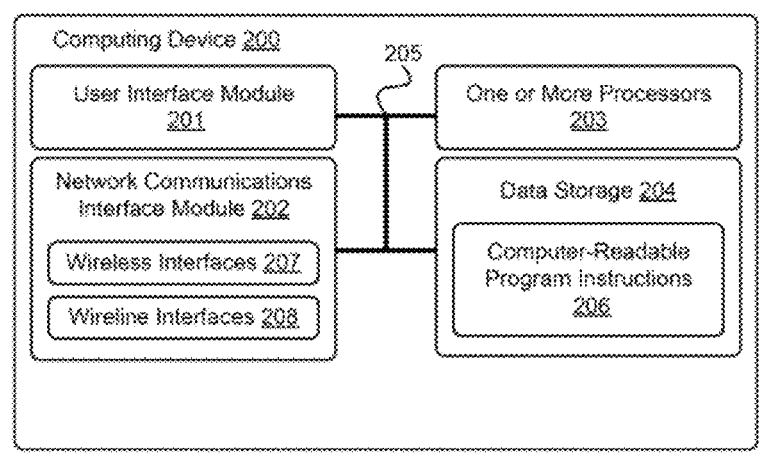
FIG. 2A is a block diagram of a computing device (e.g., system) in accordance with an example embodiment.

FIG. 2A is a block diagram of a computing device (e.g., system) in accordance with an example embodiment. In particular, computing device 200 shown in FIG. 2A can be configured to perform one or more functions of mass spectrometer 102, client device 104a, 104b, network 106, spectra identifier 108, spectra database 110, and/or stored spectra 112. Computing device 200 may include a user interface module 201, a network-communication interface module 202, one or more processors 203, and data storage 204, all of which may be linked together via a system bus, network, or other connection mechanism 205.

User interface module 201 can be operable to send data to and/or receive data from external user input/output devices. For example, user interface module 201 can be configured to send and/or receive data to and/or from user input devices such as a keyboard, a keypad, a touch screen, a computer mouse, a track ball, a joystick, a camera, a voice recognition module, and/or other similar devices. User interface module 201 can also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, either now known or later developed. User interface module 201 can also be configured to generate audible output(s), such as a speaker, speaker jack, audio output port, audio output device, earphones, and/or other similar devices.

Network-communications interface module 202 can include one or more wireless interfaces 207 and/or one or more wireline interfaces 208 that are configurable to communicate via a network, such as network 106 shown in FIG. 1. Wireless interfaces 207 can include one or more wireless transmitters, receivers, and/or transceivers, such as a Bluetooth transceiver, a Zigbee transceiver, a Wi-Fi transceiver, a WiMAX transceiver, and/or other similar type of wireless transceiver configurable to communicate via a wireless network. Wireline interfaces 208 can include one or more wireline transmitters, receivers, and/or transceivers, such as an Ethernet transceiver, a Universal Serial Bus (USB) transceiver, or similar transceiver configurable to communicate via a twisted pair, one or more wires, a coaxial cable, a fiber-optic link, or a similar physical connection to a wireline network.

In some embodiments, network communications interface module 202 can be configured to provide reliable, secured, and/or authenticated communications. For each communication described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as CRC and/or parity check values). Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms can be used as well or in addition to those listed herein to secure (and then decrypt/decode) communications.

Processors 203 can include one or more general purpose processors and/or one or more special purpose processors (e.g., digital signal processors, application specific integrated circuits, etc.). Processors 203 can be configured to execute computer-readable program instructions 206 contained in storage 204 and/or other instructions as described herein.

Data storage 204 can include one or more computer-readable storage media that can be read and/or accessed by at least one of processors 203. The one or more computer-readable storage media can include volatile and/or non-volatile storage components, such as optical, magnetic, organic or other memory or disc storage, which can be integrated in whole or in part with at least one of processors 203. In some embodiments, data storage 204 can be implemented using a single physical device (e.g., one optical, magnetic, organic or other memory or disc storage unit), while in other embodiments, data storage 204 can be implemented using two or more physical devices.

Data storage 204 can include computer-readable program instructions 206 and perhaps additional data. For example, in some embodiments, data storage 204 can store part or all of a spectra database and/or stored spectra, such as spectra database 110 and/or stored spectra 112, respectively. In some embodiments, data storage 204 can additionally include storage required to perform at least part of the herein-described methods and techniques and/or at least part of the functionality of the herein-described devices and networks.

Figure 2B:
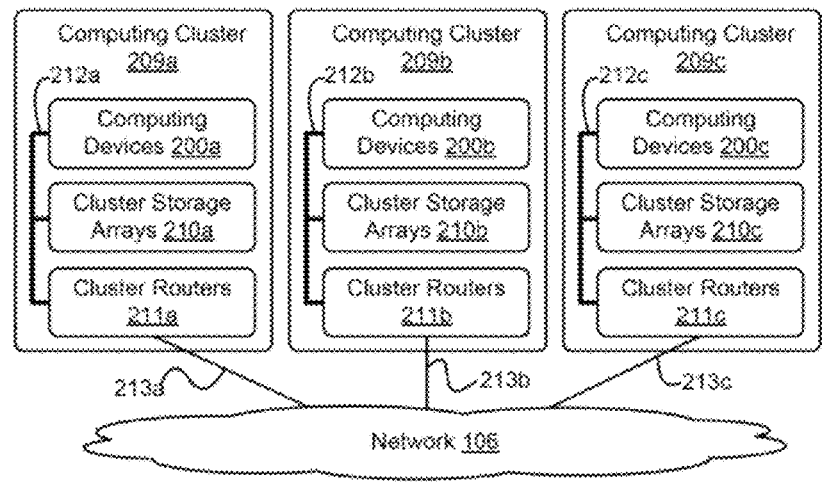
FIG. 2B depicts a network 106 of computing clusters 209a, 209b, and 209c arranged as a cloud-based server system in accordance with an example embodiment.

FIG. 2B depicts a network 106 of computing clusters 209a, 209b, 209c arranged as a cloud-based server system in accordance with an example embodiment. Spectra identifier 108 and/or spectra database 110 can be cloud-based devices that store program logic and/or data of cloud-based applications and/or services. In some embodiments, spectra identifier 108 and spectra database 110 can be a single computing device residing in a single computing center. In other embodiments, spectra identifier 108 and/or spectra database 110 can include multiple computing devices in a single computing center, or even multiple computing devices located in multiple computing centers located in diverse geographic locations. For example, FIG. 1 depicts each of spectra identifier 108 and spectra database 110 residing in different physical locations.

In some embodiments, data and services at spectra identifier 108 and spectra database 110 can be encoded as computer readable information stored in tangible computer readable media (or computer readable storage media) and accessible by client devices 104a and 104b, and/or other computing devices. In some embodiments, data at spectra identifier 108 and/or spectra database 110 can be stored on a single disk drive or other tangible storage media, or can be implemented on multiple disk drives or other tangible storage media located at one or more diverse geographic locations.

FIG. 2B depicts a cloud-based server system in accordance with an example embodiment. In FIG. 2B, the functions of spectra identifier 108 and/or spectra database 110 can be distributed among three computing clusters 209a, 209b, and 208c. Computing cluster 209a can include one or more computing devices 200a, cluster storage arrays 210a, and cluster routers 211a connected by a local cluster network 212a. Similarly, computing cluster 209b can include one or more computing devices 200b, cluster storage arrays 210b, and cluster routers 211b connected by a local cluster network 212b. Likewise, computing cluster 209c can include one or more computing devices 200c, cluster storage arrays 210c, and cluster routers 211c connected by a local cluster network 212c.

In some embodiments, each of the computing clusters 209a, 209b, and 209c can have an equal number of computing devices, an equal number of cluster storage arrays, and an equal number of cluster routers. In other embodiments, however, each computing cluster can have different numbers of computing devices, different numbers of cluster storage arrays, and different numbers of cluster routers. The number of computing devices, cluster storage arrays, and cluster routers in each computing cluster can depend on the computing task or tasks assigned to each computing cluster.

In computing cluster 209a, for example, computing devices 200a can be configured to perform various computing tasks of spectra identifier 108. In one embodiment, the various functionalities of spectra identifier 108 can be distributed among one or more of computing devices 200a, 200b, and 200c. Computing devices 200b and 200c in computing clusters 209b and 209c can be configured similarly to computing devices 200a in computing cluster 209a. On the other hand, in some embodiments, computing devices 200a, 200b, and 200c can be configured to perform different functions.

In some embodiments, computing tasks and stored data associated with server devices 108 and/or 110 can be distributed across computing devices 200a, 200b, and 200c based at least in part on the processing requirements of spectra identifier 108 and/or spectra database 110, the processing capabilities of computing devices 200a, 200b, and 200c, the latency of the network links between the computing devices in each computing cluster and between the computing clusters themselves, and/or other factors that can contribute to the cost, speed, fault-tolerance, resiliency, efficiency, and/or other design goals of the overall system architecture.

The cluster storage arrays 210a, 210b, and 210c of the computing clusters 209a, 209b, and 209c can be data storage arrays that include disk array controllers configured to manage read and write access to groups of hard disk drives. The disk array controllers, alone or in conjunction with their respective computing devices, can also be configured to manage backup or redundant copies of the data stored in the cluster storage arrays to protect against disk drive or other cluster storage array failures and/or network failures that prevent one or more computing devices from accessing one or more cluster storage arrays.

Similar to the manner in which the functions of spectra identifier 108 and/or spectra database 110 can be distributed across computing devices 200a, 200b, and 200c of computing clusters 209a, 209b, and 209c, various active portions and/or backup portions of these components can be distributed across cluster storage arrays 210a, 210b, and 210c. For example, some cluster storage arrays can be configured to store the data of spectra identifier 108, while other cluster storage arrays can store data of spectra database 110. Additionally, some cluster storage arrays can be configured to store backup versions of data stored in other cluster storage arrays.

The cluster routers 211a, 211b, and 211c in computing clusters 209a, 209b, and 209c can include networking equipment configured to provide internal and external communications for the computing clusters. For example, the cluster routers 211a in computing cluster 209a can include one or more internet switching and routing devices configured to provide (i) local area network communications between the computing devices 200a and the cluster storage arrays 201a via the local cluster network 212a, and (ii) wide area network communications between the computing cluster 209a and the computing clusters 209b and 209c via the wide area network connection 213a to network 106. Cluster routers 211b and 211c can include network equipment similar to the cluster routers 211a, and cluster routers 211b and 211c can perform similar networking functions for computing clusters 209b and 209b that cluster routers 211a perform for computing cluster 209a.

In some embodiments, the configuration of the cluster routers 211a, 211b, and 211c can be based at least in part on the data communication requirements of the computing devices and cluster storage arrays, the data communications capabilities of the network equipment in the cluster routers 211a, 211b, and 211c, the latency and throughput of local networks 212a, 212b, 212c, the latency, throughput, and cost of wide area network links 213a, 213b, and 213c, and/or other factors that can contribute to the cost, speed, fault-tolerance, resiliency, efficiency and/or other design goals of the moderation system architecture.

Example Spectrum Identification Algorithm

Figure 3A:
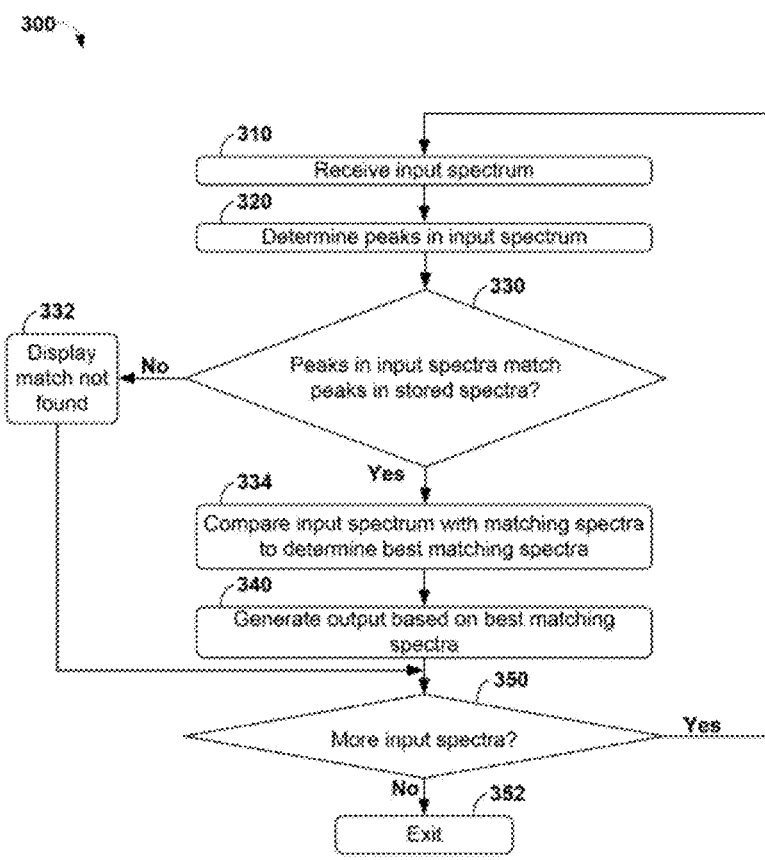
FIG. 3A shows an example method 300 for spectral identification. At block 310, an input spectrum is received.

FIG. 3A shows an example method 300 for spectral identification. At block 310, an input spectrum is received. The input spectrum can utilize any format for a spectrum, such as but not limited to utilizing a raw data format, JCAMP-DX, ANDI-MS, mzXML, mzData, and/or mzML. Other formats can be used as well or instead.

At block 320, one or more peaks in the input spectrum are identified. The peaks can be determined using the MassSpecWavelet techniques discussed above or via other techniques, such sorting the input spectrum by relative intensity or abundance and taking the top T, T>0, points in the sorted input spectrum. Other techniques can be used as well.

Figure 3B:
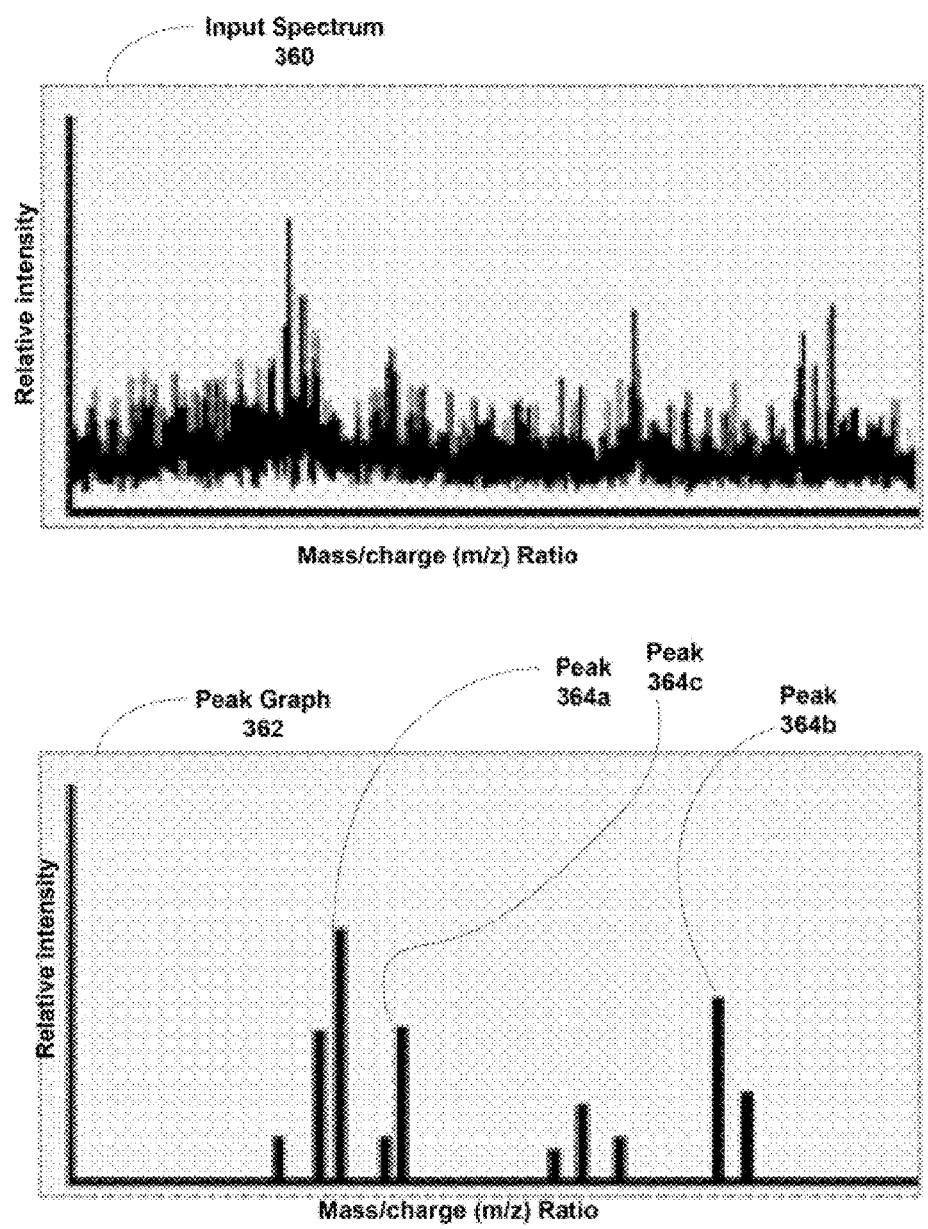
FIG. 3B shows and example input spectrum 360 and corresponding graph 362 of peaks of input spectrum 360.

FIG. 3B shows and example input spectrum 360 and corresponding graph 362 of peaks of input spectrum 360. FIG. 3B specifically identifies the three highest peaks, respectively peaks 364a, 364b, and 364c, in input spectrum 360 as displayed in peak graph 362.

Returning to FIG. 3A, at block 330, a comparison between peaks of the input spectra and peaks in one or more stored spectra is performed. The stored spectra can be stored in any format for a spectrum, such as but not limited to storage in a raw data format, JCAMP-DX, ANDI-MS, mzXML, mzData, and/or mzML. In some embodiments, the input spectrum and/or some or all of the stored spectra can be converted between formats before or during the comparison. The stored spectra can also include additional information, such as a name of a compound, molecule, structure, substance, ion, fragment, or other identifier that can be used to identify the spectrum. For example, if a stored spectrum is a spectrum for pure water, then the stored spectrum can have additional information such as "water" or "$H_2O$" to help identify the stored spectrum.

If the peaks of the input spectra match peaks in one or more stored spectra, method 300 proceeds to block 334. Otherwise, method 300 proceeds to block 332 where a "no match" display is generated and displayed. After completing the procedures of block 332, method 300 can proceed to block 350.

At block 334, the input spectrum is compared to each of the one or more matching and stored spectra identified at block 330. For example, consider spectra provided with relative intensity and mass/charge ratio values. For each of the input spectrum and the matching spectra, a dot product of the relative abundance and mass/charge value can be taken to determine a weighted average mass/charge value. Then, the weighted average mass/charge value for the input spectrum $A(IS)$ can be compared to each of the weighted average mass/charge values for the matching spectra $A(MS_i)$, where i=1 to the number of matching spectra. The matching spectra j with the closest weighted average mass/charge value $A(MS_j)$, to $A(IS)$ can be considered to be a best matching spectrum. In some embodiments, a difference between $A(MS_j)$ and $A(IS)$ can be determined, and if the absolute value of this difference is greater than a threshold, then the best matching spectrum can be considered not to match the input spectrum. If the two spectra are not considered to match, method 300 can proceed to block 332 (transfer of control not shown in FIG. 3A).

At block 340, when a match is found, an output based on the best matching spectrum can be generated. For example, if identifying information for the stored spectrum is maintained, the output can indicate an identity of the matching spectrum. Also or instead, the input spectrum and/or the matching spectrum can be shown as part of the display. Further, the $A(MS_j)$ and $A(IS)$ can be part of the display as well. Other information can be part of the display as well.

The output can be provided using some or all components of a user interface module, such as user interface module 201, and/or a network communications interface module, such as network communication interface module 202. For example, the output can be displayed on a display, printed, emitted as sound using one or more speakers, and/or transmitted to another device using network communications interface module. Other examples are possible as well.

At block 350, a determination is made as to whether there are additional input spectra to be processed. If there are additional spectra to be processed, method 300 can proceed to block 310; otherwise, method 300 can proceed to block 352, where method 300 exits.

Figure 4:
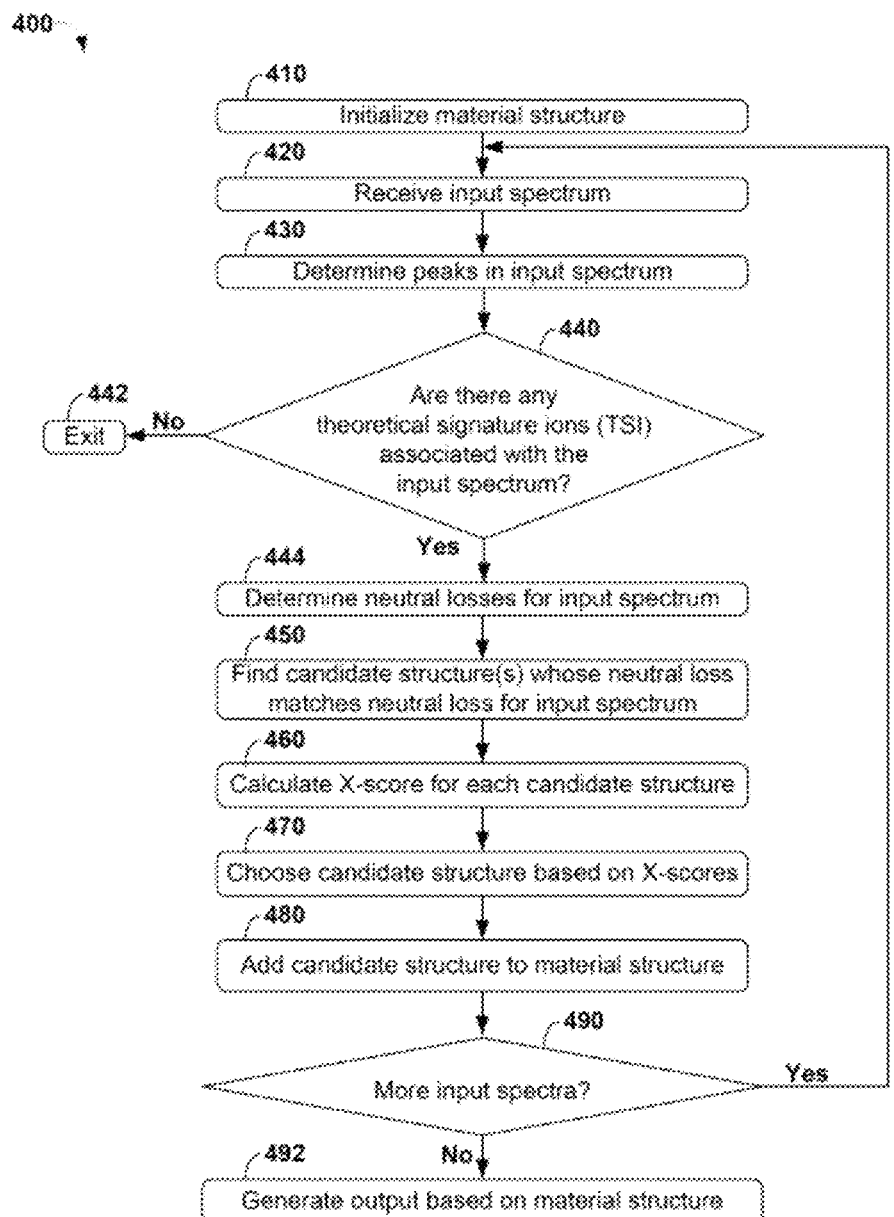
FIG. 4 shows another example method 400 for spectral identification.

FIG. 4 shows another example method 400 for spectral identification.

At block 410 of method 400, a material structure is initialized. For example, the material structure can be initialized to no structure, or, if a material in a known class of materials (e.g., lipids) are to be analyzed, the material structure can be initialized to a generic member of the known class of materials.

At block 420, an input spectrum is received. The input spectrum can be expressed in any format for a spectrum, such as but not limited to raw data format, JCAMP-DX, ANDI-MS, mzXML, mzData, or mzML. Other formats can be used as well or instead.

At block 430, one or more peaks in the input spectrum are identified. The peaks can be determined using the MassSpecWavelet techniques discussed above or via other techniques, such sorting the input spectrum by relative intensity or abundance and taking the top T, T>0, points in the sorted input spectrum. Other techniques can be used as well.

At block 440, a determination is made as to whether there are any theoretical signature ions (TSIs) associated with the input spectrum. The determination can be made via a database query or other comparison between stored data for theoretical signature ions and the identified peaks of the input spectrum. In some embodiments, data about one or more precursor ions can be stored and associated with a theoretical signature ion. In other embodiments, probability information, such as a classification score for identification, can be generated, passed in to the database as part of the database query, and used to aid identification of a theoretical signature ion.

If one or more theoretical signature ions are found to be associated with the input spectrum, then method 400 can proceed to block 444.

However, if no theoretical signature ions are found to be associated with the input spectrum, then method 400 can proceed to block 442 and exit.

At block 444, neutral losses for the input spectrum can be determined. For example, a mass of a signature ion can be calculated and used as the value of the neutral loss of the input spectrum. If multiple signature ions are determined to be associated with the input spectrum, the mass of each signature ion can be used as a neutral loss value. As another example, the stored data for the signature ion can include one or more neutral loss values, which can be used as the neutral loss value(s) for the input spectrum.

At block 450, candidate structures(s) can be found whose neutral loss matches a neutral loss for the input spectrum. For example, one or more theoretical neutral loss (TNL) values can be stored in a theoretical neutral loss database. In some embodiments, the theoretical neutral loss database can one or more records, each with a neutral loss value as a key and one or more candidate structures as attributes associated with the key neutral loss value. In these embodiments, the theoretical neutral loss database can be queried with each neutral loss value and any structure(s) retrieved by these queries can be treated as candidate structures.

At block 460, an X-score for each candidate structure can be determined. The X-score can be determined between a given candidate structure and the input spectrum using any suitable scoring scheme, including but not limited to those disclosed in the examples below. For example, an X-score calculation can be a scalar dot product between the material structure with the given candidate structure added and part or all of the input spectrum, perhaps as adjusted with a correction factor.

At block 470, the candidate structure with a best X-score can be selected as a best candidate structure.

At block 480, the material structure can be updated to include the best candidate structure.

At block 490, a determination is made as to whether there are additional input spectra to be processed. If there are additional spectra to be processed, method 400 can proceed to block 420; otherwise, method 300 can proceed to block 492.

At block 492, an output based on the material structure can be generated. The output can include the material structure, the input spectra, some or all of the candidate structures, identifying information and/or other information.

The output can be provided using some or all components of a user interface module, such as user interface module 201, and/or a network communications interface module, such as network communication interface module 202. For example, the output can be displayed on a display, printed, emitted as sound using one or more speakers, and/or transmitted to another device using network communications interface module. Other examples are possible as well.

After completing the procedures of block 492, method 400 can end.

Generating Theoretical Signature Ion and Theoretical Mass

In a second aspect, the present invention provides methods for constructing libraries of precursor ion and multiplexed mass spectra and/or $MS^n$ data for fungal lipids, such as glycerophospholipids, sphingolipids, and sterols, comprising (a) obtaining PIMS data on precursor ions for fungal lipids or precursors molecules thereof obtained from a plurality of different fungi;

(b) determining precursor ion m/z values and relative ratios of precursor ion signals relative to each other;

(c) determining consensus values for the precursor ion m/z values and the relative ratios of the precursor ion signals relative to each other for a given fungi; and (d) storing the consensus values in a database as a feature of the fungal type.

As disclosed above, the libraries of the invention can be used, for example, for the automatic identification of fungal species. Accessible information from the library can include: i) fungal species, fungal $MS^1$ phenotypes, ii) lipid hierarchical tandem mass spectra ($MS^1$ to $MS^n$), iii) annotated lipid structures, and iv) theoretical and observed isotopic distributions for the primary precursor ion species in each $MS^1$ data set All embodiments and combinations of embodiments of the first aspect of the invention can be used in this second aspect unless the context dictates otherwise. Thus, the methods for extracting/isolating fungal lipid samples from fungi include but are not limited to any of the methods disclosed herein. Similarly, all embodiments of MS devices/techniques that can be used are equally applicable in this aspect, as are the various embodiments for obtaining PIMS data and determining precursor ion m/z values and relative ratios of precursor ion signals relative to each other. In one embodiment, MALDI-TOF-MS and/or SAWN-ITMS$^n$ data in both positive and negative ion modes are used. In one non-limiting example, MALDI-TOF-MS$^1$ data is used (together with data from other MS instrument types) to populate the database with precursor ion (i.e. $MS^1$) data in positive- and negative-ion modes. These $MS^1$ data consist of two columns of numbers, m/z values and relative intensity for each. Acquiring $MS^1$ data on different platforms provide technical replicates of each extract and an understanding of how instrumental differences and operators affect fungal identification. Additionally, it permits determination of which lipid extracts only produce good data in positive ion mode.

For example, suppose two mass spectrometers MS1 and MS2 are used to generate spectra and/or other information to be stored in a database. In this example, suppose MS1 generates spectra using the JCAMP-DX format, while MS2 generates spectra using the mzXML format. Further, suppose that the database uses a third format to store spectra. The database and/or auxiliary software can convert JCAMP-DX and mzXML formatted spectra into the third format for database storage. Then, upon retrieval, the database and/or auxiliary software can reconvert the stored third-format spectra into another format, such as, but not limited to JCAMP-DX or mzXML, for output.

The methods of this aspect of the invention comprise fungal lipid samples from a plurality (2 or more) of different fungi. The number of different fungi from which samples are obtained is determined based on user needs. In various embodiments, PIMS data may be obtained from/resulting data stored for two or more different fungi. As used herein, "different fungi" are different fungal species, different sub-species, and/or the same species/sub-species but where some portion has undergone an environmental modification (for example, development of antifungal resistance).

In one embodiment, PIMS data may be obtained from one, two, three, four, or more (or all) of the following genera of fungi, species of such genera, or sub-species of such genera: *Candida, Aspergillus, Rhyzopus, Cryptococcus, Histoplasma, Pneumocystis, Stachybotrys, Sporothrix, Trichophyton, Microsporum, Blastomyces, Mucoromycotina, Coccidioides, Exserohilum, Cladosporium, Coccoides, Encephalitozoon, Encephalitozoon, Fusarium, Lichtheimia, Mortierella, Malassezia, Prototheca, Pythium, Rhodotorula, Fusarium, Thielaviopsis, Verticillium, Magnaporthe, Sclerotinia, Ustilago, Rhizoctonia, Puccinia, Armillaria, Botrytis, Blumeria, Mycosphaerella, Colletotrichum, Melampsora, Saprolegniasis, Ichthyosporidium, Exophiala,*

Branchiomycosis, and *Penicillium*. Representative fungal species include *Histoplasma capsulatum, Blastomyces dermatitidis, Coccidioides immitis, Paracoccidioides brasiliensis, Aspergillus fumigatus, Candida albicans, Cryptococcus neoformans, Magnaporthe grisea, Sclerotinia sclerotiorum, Phakospora pachyrhizi* and *Botrytis cinerea*.

In another embodiment, the methods further comprise fragmenting all or a subset of the precursor ions to produce a set of derived fragment ions, and obtaining mass spectra on all or a subset of the derived fragment ions ($MS^n$ or multiplexed ion) spectra; determining consensus values for the derived fragment ion m/z values and the relative ratios of the derived fragment ion signals relative to each other for a given fungus; and storing the consensus values as a feature of the fungus type in a database. "Derived fragment ions" are described above; all embodiments for obtaining and analyzing $MS^n$ and or multiplexed ion spectra herein are applicable to this third aspect of the invention. In one embodiment, the $MS^n$ spectra data is obtained for at least two generations, $MS^1$ and $MS^2$, of precursor ions ($MS^1$) and derived fragment ions ($MS^2$); in another embodiment, at least three generations $MS^1$, $MS^2$, and $MS^3$, of precursor ions ($MS^1$) and derived fragment ions ($MS^2$ and $MS^3$); etc.

In one non-limiting example, SAWN-ITMS$^n$ data is obtained. Subtle details of strain variation resulting from environmental pressure may be hidden under $MS^1$ isobaric signals. Use of the $MS^n$ approach helps to tease apart all lipid structures above a threshold, including those highly similar isobars obscured in $MS^1$ data as a single m/z species. In one embodiment, the threshold is preset threshold. Any suitable threshold can be used, and it is within the level of those of skill in the art to establish a suitable threshold, based on the teachings herein. In one non-limiting embodiment, the threshold would require a minimum signal/noise ratio of 2:1. See, for example, *Anal. Chem.* 81:6481-8 (2009). For lipid structure definition the SAWN-ITMS$^n$ platform can be used to acquire positive- and negative-ion $MS^1$ and $MS^n$ data. The $MS^n$ data can be generated for the most abundant ion species (approximately 5-7 species) in each $MS^1$ spectrum and their structures determined using the $MS^n$ methods described in detail above. Structures and all SAWN-ITMS1 and SAWN-ITMS$^n$ data can be recorded in the MSGS library to identify fungi alone, or in combination with MALDI-TOF-$MS^1$ data.

In another embodiment, the methods further comprise storing in the database as a feature of the fungal type one or more of signature ions, and lipid structure(s). Signature ions can be determined via standard MS techniques based on the teachings herein; signature ions for some fungal lipids that are known may be input into the database, for example, manually or through automated access to other databases. Similarly, fungal lipid structures can be determined using the methods of the present invention; previously identified fungal lipid structures may also be input into the database, for example, manually or through automated access to other databases.

In another embodiment, the method comprises storing consensus values for the precursor ion and derived fragment ion m/z values and the relative ratios of the precursor ion derived fragment ion signals relative to each other for a given fungus in a theoretical neutral loss database, wherein the consensus values are used to assign a dissociation formula for fungal lipids for the different fungal types. As used herein, dissociation formulae are the pathway(s) of dissociation of a precursor ion. In this embodiment, the method results in a database comprising, for example, a database based on the interpretation of fungal lipid fragmentation rules in tandem mass spectra which includes phosphate patterns as well as fatty acid and monosaccharide substituents. Direct bond cleavages of fungal lipid structures can be considered as the general template for fragmentation and structural inference. In a further embodiment, each database may comprise two sub-databases (or may comprise two separate but connected databases) for: (1) theoretical signature ions (TSI) and (2) theoretical neutral losses (TNL).

To increase the structural diversity of fungal lipids represented in the TSI database, a user-defined carbon range of fatty acids can be applied (for example, 12:0 to 20:0 fatty acids). By systematically altering the fatty acid side chain lengths and positions, all possible signature ions can be computed, if desired, and incorporated into the TSI database. To facilitate structure assignment, neutral losses of signature ions can be calculated and put in the theoretical neutral loss (TNL) database. Additionally, common observed neutral losses that come from direct bond cleavages of fungal lipids other than cleavages of signature ions can also be included in the TNL database. Similarly, to increase the structural diversity covered by TNL databases, fatty acid compositions of TNL can be systematically altered within the user-defined carbon range.

In this embodiment, acquired $MS^n$ data for an unknown fungi can be searched against the TSI database to find possible signature ions. Any identified signature ions suggest formulae corresponding to the reducing and/or non-reducing portions of the lipid. By subtracting the mass of signature ions from their precursors, the neutral losses of signature ions can be subsequently calculated and searched against the TNL database. The combination of signature ions and matched neutral losses may be used to provide a preliminary candidate structure.

The library structure and reading software can be of any suitable type. In one non-limiting embodiment, the library structure software may be based, for example, on a relational database system (MySQL), and the reading software can be a graphical user interface, such as a web-based user interface. The library can be stored in a MySQL database hosted on a desired secure server. The library structure software is geared toward extracting information from the library for fungal identification by processing queries for comparison of observed data to previously recorded data. In other embodiments, the library structure software can provide some or all data stored in the theoretical signature ion (TSI) and/or theoretical neutral loss (TNL) database to an application program for processing without use of database queries. For information on the open source software MySQL concept see the articles describing it at web site dev.mysql.com/tech-resources/articles/.

EXAMPLES

Extraction Protocol

Fungal membrane lipids, including glycerophospholipids, sphingolipids, and sterols (FIG. 5) were prepared using a published isolation method (*J. Lipid Res.* 46: 1773-1778, (2005)). Briefly, approximately 0.1-10 mg of material from an overnight culture grown on solid medium (e.g. appropriate agar plate) of a selected strain was resuspended in 400 µl of isobutyric acid and 1 M ammonium hydroxide (5:3 v:v) in a 1.5 ml screw-cap test tube, incubated at 100° C. for 30 minutes to 1 h with frequent vortexing. Individual samples were cooled in ice water and centrifuged for 15 min at 2000×g, supernatants were collected and diluted 1:1 (v:v) with endotoxin-free water. The samples were subsequently frozen and lyophilized overnight. The resultant powered material was washed twice with 1 ml of methanol and the insoluble fungal lipids were extracted in 100-200 µl of a mixture of chloroform, methanol, and water (3:1:0.25 v:v:v) depending on the starting amount.

Mass Spectrometry Procedures

Negative ion matrix assisted laser ionization desorption-time of flight tandem mass spectrometry (MALDI-TOF/TOF MS) experiments was performed (*Glycoconjugate J.* 5:397-409 (1988); *Mol Microbiol* 52(5):1363-73 (2004)). Briefly, fungal lipids were solubilized in 200 µl of a mixture of chloroform, methanol, and water (3:1:0.25 v:v:v) and spotted (1 µL) directly onto the MALDI sample plate, followed by 1 µL of 100 mg/mL norharmane MALDI matrix dissolved in chloroform/methanol/water (3:1.5:0.25, v/v/v). All experiments were performed using a Bruker Autoflex Speed MALDI-TOF/TOF mass spectrometer (Bruker Daltonics Inc., Billerica, Mass., USA). Each spectrum was an average of 300-500 shots and 50-75% laser power.

For MS/MS analysis, precursor ions were chosen and submitted for LIFT TOF/TOF acquisition in the negative ion mode as per Bruker standard MALDI-TOF protocols. ES Tuning Mix (Agilent, Palo Alto, Calif., USA) was used as a calibration standard.

MALDI-TOF Mass Spectra of Fungal Lipid Extracts

MS1 spectra were collected and preprocessed as follows. Raw data files were converted to mzXML data format. The peak list information were detected using MassSpecWavelet, a wavelet-based mass spectrum processing software provided by the Bioconductor (*Bioinformatics* 22(17):2059-2065 (2006)). The similarity of pairs of the spectra was determined by calculating their dot-product.

Figure 6:
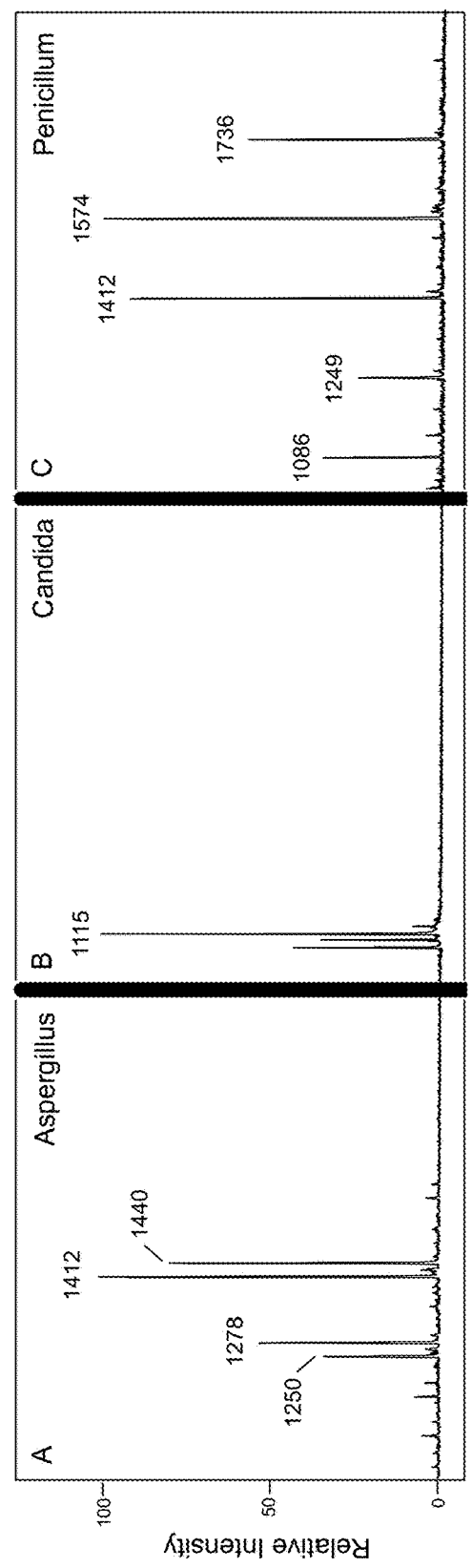
FIG. 6 shows representative mass spectra from fungi. Shown are: (A) *Aspergillus,* (B) *Candida,* and (C) *Penicillium* species. Lipid extracts generated using a small-scale lipid extraction method and mass spectra recorded in negative ion mode on a MALDI-TOF-MS (Bruker Autoflex).

Spectra shown in FIG. 6 are representative examples for three fungal backgrounds. Using these methods of lipid extraction and MS analysis, the results from the three fungal species were used to generate the heat map demonstration of lipid phenotyping (FIG. 7).

This data clearly demonstrates the ability of fungal lipid MS1 data to distinguish different pathogenic and environmental fungal species. As indicated by the diagonal black set of squares in FIG. 7, all data sets most closely match themselves and not other data. The black squares represent a normalized score of 1.0 or a perfect match, while the dark gray squares represent a score of 0 at the opposite end of the normalized scoring scheme or where there is no match. Intermediate gray color (no shown) indicates that there is high similarity, but that there are MS features remaining that distinguish these data as unique one from the other. Direct speciation of fungal background demonstrates that this approach will succeed where the protein phenotype of Biotyper fails.

This data set demonstrates that fungi may be identified by MS1 profiles of their lipid extracts. To provide more objective evidence of the value of this approach, sensitivity (100%), accuracy (96%), and specificity (96%) were calculated using a standard receiver operating characteristic (ROC) curve and a 6-point result rating (data not shown).

Manual Structural Analysis of Fungal Lipids

Fungal lipid structural diversity is reflected, in part, in the complexity of the lipids present in the membrane that includes, but is not limited to, glycerophospholipids, sphingolipids, and sterols. Within these classes of lipids, complexity is observed in the various combinations of fatty acids (numbers and types), head groups present (phosphocholine, phosphoethanolamine), and the presence of simple or complex carbohydrate residues attached to the base lipid molecule. Significant complexity in extractable lipids is observed in fungal lipids extracted for *Penicillium, Candida,* and *Aspergillus* as shown for FIG. 5. For *Penicillium*, the observed periodicity of Δm/z 162 suggests the addition of six carbon sugar moieties, whereas the differences in *Aspergillus* represent heterogeneity in both the number of fatty acids present and the length of the fatty acids (Δm/z28 $C_2H_4$). Finally, *Candida* shows low complexity but lipid molecules that are significantly small than either fungal species.

Theoretical Databases Construction

A theoretical database constructor program will be written with Perl v5.8.8 (http://www.perl.org) built for x86_64-Linux platform. A species-specific theoretical database will be constructed based on the manual interpretation of lipid fragmentation rules in tandem mass spectra which will include phosphate patterns as well as fatty acid and monosaccharide substituents. Direct bond cleavages of lipid structures will be considered as the general template for fragmentation and structural inference.

Each species-specific theoretical database contains two sub-databases for: 1) theoretical signature ions (TSI) and 2) theoretical neutral losses (TNL). Observed signature ions are unique ions that help hypothesize the molecule's structure. The observed fungal lipid signature ions will usually be determined from the conserved characteristic of lipids and named according to the nomenclature described by Domon and Costello (*Glycoconjugate J.* 5:397-409 (1988)). Based on the observed fragmentation templates of the lipids, signature ions were calculated and put into the theoretical signature ion (TSI) database. To increase the structural diversity of the lipids represented in the TSI database, a user-defined carbon range of fatty acids will be applied (i.e. 12:0 to 20:0 fatty acids). By systematically altering the fatty acid side chain lengths and positions, all possible signature ions will be computed and incorporated into the TSI database. To facilitate the structure assignment, neutral losses of signature ions will also be calculated and put in the theoretical neutral loss (TNL) database. Additionally, common observed neutral losses that come from direct bond cleavages of the lipids other than cleavages of signature ions will also be included in the TNL database. Similarly, to increase the structural diversity covered by TNL databases, fatty acid compositions of TNL will be systematically altered within the user-defined carbon range.

DeltaMass

DeltaMass is a user assigned HiTMS parameter that defines the mass tolerance used to represent the acceptable mass difference between theoretical and observed ions. DeltaMass will be applied in all searches against the TSI and TNL databases using the values consistent with the mass accuracy of the acquired data.

Data Preprocessing

Raw data files will be converted into mzXML data format by ReAdW, available in Xcalibur software (Thermo Scientific). The peak information from either individual or averaged mass spectra will then be extracted using MassSpecWavelet, a wavelet transform based peak detection software provided by the Bioconductor project (http://www.bioconductor.org/) (*Bioinformatics* 22 (17):2059-65 (2006)). Resulting peak information of each MS$^n$ tandem mass spectrum will be recorded in a peak list file (referred as MS$^n$ spectra hereafter).

Hierarchical Tandem Mass Spectrometry (HiTMS) Algorithm

HiTMS will be implemented in Perl v5.8.8 (http://www.perl.org) and run on a 64-bit GNU/Linux platform. Acquired MS$^n$ spectra will be searched against TSI database to find possible signature ions, and spectra without any identifiable signature ions will be discarded. Any identified signature ions will suggest formulae corresponding to the reducing and/or non-reducing portions of fungal lipids. By subtracting the mass of signature ions from their precursors, the neutral losses of signature ions will be subsequently calculated and searched against the TNL database. The combination of signature ions and matched neutral losses will provide a preliminary candidate structure. The calculated neutral losses of all the ions in each spectrum will also be searched against the TNL database to provide needed information for spectrum annotation. To each lipid-spectrum match (LSM) an X-score will be applied to evaluate the closeness of fit between every $MS^n$ spectrum and its preliminary candidate structures (see Cross Correlation). After preliminary structures are assigned, neutral loss of every $MS^n$ spectrum's precursor ion will be calculated in the corresponding $MS^{n-1}$ spectrum and searched against TNL database again to identify the possible dissociation patterns. HiTMS will continue the above procedures in an iterative manner until the $MS^1$ level is reached. The final structures will be deduced by integrating the information gained from the different levels of $MS^n$ data.

Cross Correlation (X-Score)

The X-score uses a closeness of fit measurements between an acquired and theoretical tandem mass spectrum similar to SEQUEST xcorr (*J Am Soc Mass Spectrom* 5(11): 976-989 (1994); *J Proteome Res* 7(10):4598-602 (2008)). For every LSM, hypothetical lipid structure is fragmented in silico based primarily on aforementioned direct bond cleavages, including glycosidic bond cleavages (i.e. A/X, B/Y, C/Z type ions), losses of 0- and N-linked acyl chains, losses of phosphate, losses of monosaccharide and perturbations representing combined losses. Fragmentations will then be combined into a reconstructed mass spectrum representing the theoretical dissociation of the candidate structure. The peak intensity of each reconstructed mass spectrum will be assigned a Boolean value where 1 represents the existence of a fragmentation of such m/z value. The X-score between the acquired mass spectrum and the reconstructed mass spectrum of hypothetical structure is measured as follows:

$$X - \text{score} = x_0 \cdot y' \text{ where } y' = y_0 - \left(\sum_{\tau=-75, \tau \neq 0}^{\tau=+75} y_\tau\right)/150$$

Each X-score calculation will be a scalar dot product between reconstructed mass spectrum x and the preprocessed acquired mass spectrum y' where $\tau$ is the correction factor, as described in previous publications (*J Am Soc Mass Spectrom* 5(11): 976-989 (1994); *J Proteome Res* 7(10): 4598-602 (2008)). DeltaMass will be used as the bin size to convert mass spectra into vectors. X-score will be used by HiTMS to measure the closeness of fit of every LSM.

On-the-Fly Decoy Generation

In the world of proteomics, a decoy database is often employed to help evaluate the significance of peptide spectra matches. A decoy database comprises protein sequences that have been shuffled or reversed, generated from the given target database beforehand or on-the-fly (*J Am Soc Mass Spectrom* 13(4):378-86 (2002); *J Proteome Res* 5(3):695-700 (2006); *J Proteome Res* 7(7):3022-7 (2008)). HiTMS uses this target-decoy strategy, generating decoys by shuffling the candidate lipid structure on-the-fly while analyzing each $MS^n$ spectrum. To avoid destroying the lipid biochemistry, shuffling only occurs on the position and length of fatty acid side chains. This approach ensures that every decoy lipid exhibits precisely the same molecular composition and mass as the target (i.e. candidate) lipid structures. X-score of both candidate and decoy LSM are then calculated to help evaluate the significance.

We claim:

1. A method for identifying fungi by species in a sample, comprising
    (a) obtaining precursor ion mass spectra (PIMS) data on precursor ions for one or more lipids selected from the group consisting of (i) a fungal glycerophospholipid, (ii) a fungal sphingolipid, (iii) a fungal sterol, and (iv) precursors molecules thereof, from a sample containing fungi of interest;
    (b) comparing the PIMS data to a counterpart database of (i) fungal glycerophospholipid PIMS data, (ii) fungal sphingolipid PIMS data, (iii) fungal sterol PIMS data, and/or (iv) precursor molecule PIMS data;
    wherein the comparing is used to identify fungi by species in the sample.

2. The method of claim 1, wherein the comparing comprises comparing precursor ion m/z values and relative abundance of the precursor ions to the database of glycerophospholipid, sphingolipid, sterol, or precursor molecule PIMS data.

3. The method of claim 1, further comprising fragmenting all or a subset of the precursor ions to produce a multiplexed set of ions, and obtaining mass spectra on all or a subset of the multiplexed set of ions (multiplexed mass spectra data), and wherein the comparing further comprises comparing the multiplexed mass spectra data to one or more of fungal glycerophospholipid, sphingolipid, sterol, or precursor molecule multiplexed mass spectra data in the database to assist in identifying fungi by species in the sample.

4. The method of claim 1, further comprising fragmenting all or a subset of the precursor ions to produce a set of derived fragment ions, and obtaining mass spectra on all or a subset of the derived fragment ions ($MS^n$ data), and wherein the comparing further comprises sequentially comparing the $MS^n$ data to one or more of fungal glycerophospholipid, sphingolipid, sterol, or precursor molecule $MS^n$ data in the database to assist in identifying fungi by species in the sample.

5. The method of claim 4, further comprising searching the precursor ion and/or $MS^n$ data against a database of fungal glycerophospholipid, sphingolipid, sterol, and precursor molecule signature ions to identify signature ions in the precursor ion and/or $MS^n$ data.

6. The method of claim 5, further comprising
    (i) searching neutral losses of signature ions in the $MS^n$ data against a theoretical neutral loss database to identify dissociation formulae;
    (ii) proposing glycerophospholipid, sphingolipid and/or sterol candidate structures from fungi in the sample based on the dissociation formulae and the signature ions in the $MS^n$ data;
    (iii) assigning a score to each glycerophospholipid, sphingolipid and/or sterol candidate structure based on correlation between theoretical and acquired $MS^n$ data, wherein candidate structures that meet or exceed a user-defined threshold are considered as accurate assignments.

7. The method of claim 6, wherein step (i) comprises
    (A) determining a neutral loss of every $MS^n$ spectrum's precursor ion in the corresponding $MS^{n-1}$ spectrum and searching against the theoretical neutral loss database; and (B) iteratively repeating step (A) until level MS" is reached; and wherein step (ii) comprises proposing the glycerophospholipid, sphingolipid and/or sterol structures from the fungi in the sample based on the integrating data from each MS" level.

8. The method of claim 6, wherein step (iii) comprises (A) fragmenting the glycerophospholipid, sphingolipid and/or sterol candidate structures by direct bond cleavage to produce fragmentations;

(B) combining the fragmentations into a reconstructed mass spectra representing the theoretical dissociation of the glycerophospholipid, sphingolipid and/or sterol candidate structures; and (C) assigning the score to each of the glycerophospholipid, sphingolipid and/or sterol candidate structure based on correlation between theoretical MS" spectra and the reconstructed mass spectra.

9. The method of claim 1, further comprising (c) obtaining mass spectra data on precursor ions for fungal proteins in the sample;

(d) comparing the protein mass spectra data to a database of fungal protein precursor ion mass spectra data;

wherein the comparing is used to help identify fungi by species in the sample.

10. The method of claim 1, wherein the fungal glycerophospholipid is a fungal membrane glycerophospholipid, wherein the fungal sphingolipid is a fungal membrane sphingolipid, and wherein the fungal sterol is a fungal membrane sterol.

11. The method of claim 1, wherein the sample contains a single fungal species.

12. The method of claim 1, wherein the sample contains two or more fungal species.

13. The method of claim 1, wherein the fungi is a species of a fungal genera selected from the group consisting of *Candida, Aspergillus, Rhyzopus, Cryptococcus, Histoplasma, Pneumocystis, Stachybotrys, Sporothrix, Trichophyton, Microsporum, Blastomyces, Mucoromycotina, Coccidioides, Exserohilum, Cladosporium, Coccoides, Encephalitozoon, Encephalitozoon, Fusarium, Lichtheimia, Mortierella, Malassezia, Prototheca, Pythium, Rhodotorula, Fusarium, Thielaviopsis, Verticillium, Magnaporthe, Sclerotinia, Ustilago, Rhizoctonia, Puccinia, Armillaria, Botrytis, Blumeria, Mycosphaerella, Colletotrichum, Melampsora, Saprolegniasis, Ichthyosporidium, Exophiala, Branchiomycosis,* and *Penicillium.*

14. The method of claim 1, wherein the fungi is a fungal species selected from the group consisting of *Histoplasma capsulatum, Blastomyces dermatitidis, Coccidioides immitis, Paracoccidioides brasiliensis, Aspergillus fumigatus, Candida albicans, Cryptococcus neoformans, Magnaporthe grisea, Sclerotinia sclerotiorum, Phakospora pachyrhizi* and *Botrytis cinerea.*

\* \* \* \* \*